United States Patent
Crawford

(10) Patent No.: US 11,254,752 B2
(45) Date of Patent: Feb. 22, 2022

(54) METHODS FOR TREATING CANCER WITH BISPECIFIC ANTI-CD3XMUC16 ANTIBODIES AND ANTI-PD-1 ANTIBODIES

(71) Applicant: Regeneron Pharmaceuticals, Inc., Tarrytown, NY (US)

(72) Inventor: Alison Crawford, Dobbs Ferry, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 175 days.

(21) Appl. No.: 16/447,067

(22) Filed: Jun. 20, 2019

(65) Prior Publication Data

US 2019/0389966 A1    Dec. 26, 2019

Related U.S. Application Data

(60) Provisional application No. 62/688,251, filed on Jun. 21, 2018.

(51) Int. Cl.

| | |
|---|---|
| *C07K 16/30* | (2006.01) |
| *A61P 35/00* | (2006.01) |
| *A61K 39/395* | (2006.01) |
| *A61K 45/06* | (2006.01) |
| *C07K 16/28* | (2006.01) |
| *C07K 16/46* | (2006.01) |
| *A61K 39/00* | (2006.01) |

(52) U.S. Cl.
CPC ...... *C07K 16/3092* (2013.01); *A61K 39/3955* (2013.01); *A61K 39/39558* (2013.01); *A61K 45/06* (2013.01); *A61P 35/00* (2018.01); *C07K 16/2809* (2013.01); *C07K 16/2818* (2013.01); *C07K 16/468* (2013.01); *A61K 2039/505* (2013.01); *A61K 2039/545* (2013.01); *C07K 2317/31* (2013.01)

(58) Field of Classification Search
CPC ............ C07K 16/3092; C07K 16/2809; A61K 39/3955; A61K 45/06
See application file for complete search history.

(56) References Cited

U.S. PATENT DOCUMENTS

2015/0203579 A1* 7/2015 Papadopoulos ........... A61P 7/06
424/142.1

FOREIGN PATENT DOCUMENTS

| WO | 17/053856 A1 | 3/2017 | |
|---|---|---|---|
| WO | 17/197259 A1 | 11/2017 | |
| WO | WO-2018067331 A * | 4/2018 | ............ C07K 16/44 |
| WO | 18/099539 A1 | 6/2018 | |

OTHER PUBLICATIONS

Braly et al., The Immune Adjuvant Properties of Front-line Carboplatin-Paclitaxel: A Randomized Phase 2 Study of Alternative Schedules of Intravenous Oregovomab Chemoimmunotherapy in Advanced Ovarian Cancer, J Immunother. 32, 1, 54-65, Publication Date: Jan. 2009 (Year: 2009).*

Byrne et al., "A tale of two specificities: bispecific antibodies for therapeutic and diagnostic applications" Trends in Biotechnology, vol. 31 (No. 11):621-632 (2013).

ClinicalTrials.gov, "Study of REGN4018 Administered Alone or in Combination with Cemiplimab in Patients with Recurrent Ovarian Cancer," US National Library of Medicine, Trial Identifier: NCT03564340 (2018). [Retrieved from the Internet Mar. 10, 2020: <URL: https://clinicaltrials.gov/ct2/show/NCT03564340>].

Crawford et al., "A Mucin 16 bispecific T cell-engaging antibody for the treatment of ovarian cancer," Science Translational Medicine, vol. 11:1-13, (2019).

Disis et al., Abstract "Avelumab (MSB0010718C), an anti-PD-L1 antibody, in patients with previously treated, recurrent or refractory ovarian cancer: A phase lb, open-label expansion trial" American Society of Clinical Oncology (2015). [Retrieved from the Internet Mar. 12, 2020: <URL: https://ascopubs.org/doi/abs/10.1200/jco.2015.33.15_suppl.5509>].

Guo et al., "Combined Trabectedin and anti-PD1 antibody produces a synergistic antitumor efffect in a murine model of ovarian cancer," Journal of Translational Medicine vol. 13 (No. 247), 13 pages, (2015).

Guo et al., "PD-1 Blockade and OX40 Triggering Synergistically Protects against Tumor Growth in a Murine Model of Ovarian Cancer," PLOS ONE vol. 9 (No. 2), 10 pages, (2014).

Hamanishi et al., "PD-1/PD-L1 blockade in cancer treatment: perspectives and issues," Int J. Clin. Oncol. vol. 21:462-473, (2016).

Hamanishi et al., "Programmed cell death 1 ligand 1 and tumor-infiltrating CD8+ T lymphocytes are prognostic factors of human ovarian cancer," PNAS vol. 104 (No. 9):3360-3365, (2007).

Hamanishi et al., "Safety and Antitumor Activity of Anti-PD-1 Antibody, Nivolumab, in Patients with Platinum-Resistant Ovarian Cancer," Journal of Clinical Oncology, vol. 33 (No. 34), 13 pages, (2015).

Imai et al., "Express of multiple immune checkpoint molecules on T cells in malignant ascites from epithelial ovarian carcinoma," Oncology Letters, vol. 15:6457-6468, (2018).

(Continued)

*Primary Examiner* — Peter J Reddig
*Assistant Examiner* — Cheng Lu
(74) *Attorney, Agent, or Firm* — Schwabe, Williamson & Wyatt PC; Veronica Mallon

(57) ABSTRACT

The present invention provides methods for treating, reducing the severity, or inhibiting the growth of cancer (e.g., ovarian cancer or pancreatic cancer). The methods of the present invention comprise administering to a subject in need thereof a therapeutically effective amount of an antibody or antigen-binding fragment thereof that specifically binds to programmed death 1 (PD-1) receptor in combination with a therapeutically effective amount of a bispecific antibody that specifically binds Mucin 16 (MUC16) and CD3.

22 Claims, 3 Drawing Sheets

Specification includes a Sequence Listing.

(56) References Cited

OTHER PUBLICATIONS

Krah et al., "Engineering bispecific antibodies with defined chain pairing," New Biotechnology, vol. 39:167-173, (2017).
Lameris et al., "Bispecific antibody platforms for cancer immunotherapy," Critical Review in Oncology/Hematology, vol. 92:153-165, (2014).
Liu et al., "Elevated Serum Level of CA125 is a Biomarker that Can be Used to Alter Prognosis Determined by BRCA Mutation and Family History in Ovarian Cancer," Genetic Testing and Molecular Biomarkers, vol. 21 (No. 9):247-554, (2017).
Lu et al., "Combined PD-1 blockade and GITR triggering induce a potent antitumor immunity in murine cancer models and synergizes with chemotherapeutic drugs," Journal of Translational Medicine vol. 12 (No. 36), 11 pages, (2014).
Maine et al., "Programmed death ligand-1 over-expression correlates with malignancy and contributes to immune regulation in ovarian cancer," Cancer Immunol Immunother vol. 63:215-224, (2014).
Nunez-Prado et al., "The coming of age of engineered multivalent antibodies," Drug Discovery Today, vol. 20 (No. 5), 7 pages, (2015).
Spiess et al., "Alternative molecular formats and therapeutic applications for bispecific antibodies," Molecular Immunology, vol. 67:95-106, (2015).
Varga et al., Abstract "Pembrolizumab in patients with programmed death ligand 1-positive advanced ovarian cancer: Analysis of KEYNOTE-028," Gynecol. Oncol. vol. 152 (No. 2):243-250, (2019).
Weber et al., "Toxicities of Immunotherapy for the Practitioner," Journal of Clinical Oncology, vol. 33 (No. 18), 9 pages, (2015).
Wei et al., "Combinatorial PD-1 Blockade and CD137 Activation Has Therapeutic Efficacy in Murine Cancer Models and Synergizes with Cisplatin," PLOS ONE vol. 8 (No. 12), 11 pages, (2013).
WIPO Application No. PCT/US2019/038163, PCT International Search Report and Written Opinion of the International Searching Authority dated Oct. 21, 2019.
Wu et al., "T cel engaging bispecific antibody (T-BsAb): From technology to therapeutics," Pharmacology and Therapeutics vol. 182:161-175, (2018).
Zhukovsky et al., "Bispecific antibodies and CARs: generalized immunotherapeutics harnessing T cell redirection," Current Opinion in Immunology, vol. 40:24-35, (2016).
U.S. Appl. No. 62/688,251, filed Jun. 21, 2018, Expired.
PCT/US2019/038163, filed Jun. 20, 2019, WO 2019/246356, Published.

\* cited by examiner

METHODS FOR TREATING CANCER WITH BISPECIFIC ANTI-CD3XMUC16 ANTIBODIES AND ANTI-PD-1 ANTIBODIES

CROSS-REFERENCE TO RELATED APPLICATIONS

This application claims the benefit under 35 USC § 119(e) of U.S. Provisional Application No. 62/688,251, filed Jun. 21, 2018, which is incorporated herein by reference in its entirety for all purposes.

REFERENCE TO A SEQUENCE LISTING

This application incorporates by reference the Sequence Listing submitted in Computer Readable Form as file 10469US01-Sequence.txt, created on Jun. 12, 2019 and containing 33,567 bytes.

FIELD OF THE INVENTION

The present invention relates to methods for treating cancer comprising administering to a subject in need thereof a therapeutically effective amount of an antibody that specifically binds to programmed death 1 (PD-1) receptor in combination with a bispecific antibody that binds to mucin 16 (MUC16) and CD3.

BACKGROUND

Mucin 16 (MUC16), also known as cancer antigen 125, carcinoma antigen 125, carbohydrate antigen 125, or CA-125, is a single transmembrane domain highly glycosylated integral membrane glycoprotein that is highly expressed in ovarian cancer. MUC16 consists of three major domains: an extracellular N-terminal domain, a large tandem repeat domain interspersed with sea urchin sperm, enterokinase, and agrin (SEA) domains, and a carboxyl terminal domain that comprises a segment of the transmembrane region and a short cytoplasmic tail. Proteolytic cleavage results in shedding of the extracellular portion of MUC16 into the bloodstream. MUC16 is overexpressed in cancers including ovarian cancer, breast cancer, pancreatic cancer, non-small-cell lung cancer, intrahepatic cholangiocarcinoma-mass forming type, adenocarcinoma of the uterine cervix, and adenocarcinoma of the gastric tract, and in diseases and conditions including inflammatory bowel disease, liver cirrhosis, cardiac failure, peritoneal infection, and abdominal surgery. (Haridas, D. et al., 2014, *FASEB J.*, 28:4183-4199). Expression on cancer cells is shown to protect tumor cells from the immune system. (Felder, M. et al., 2014, *Molecular Cancer*, 13:129) Methods for treating ovarian cancer using antibodies to MUC16 have been investigated. Oregovomab and abgovomab are anti-MUC16 antibodies which have had limited success. (Felder, supra, Das, S. and Batra, S. K. 2015, *Cancer Res.* 75:4660-4674.)

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells. In addition, bispecific antibodies that are capable of binding CD3 and a target antigen have been proposed for therapeutic uses involving targeting T cell immune responses to tissues and cells expressing the target antigen.

Programmed death-1 (PD-1) receptor signaling in the tumor microenvironment plays a key role in allowing tumor cells to escape immune surveillance by the host immune system. Blockade of the PD-1 signaling pathway has demonstrated clinical activity in patients with multiple tumor types, and antibody therapeutics that block PD-1 (e.g., nivolumab and pembrolizumab) have been approved for the treatment of metastatic melanoma and metastatic squamous non-small cell lung cancer. Recent data has demonstrated the clinical activity of PD-1 blockade in patients with aggressive NHL and Hodgkin's lymphoma (Lesokhin, et al. 2014, Abstract 291, 56th ASH Annual Meeting and Exposition, San Francisco, Calif.; Ansell et al. 2015, *N. Engl. J. Med.* 372(4):311-9).

Ovarian cancer is the most lethal of the gynecologic malignancies; although the estimated number of new cases of ovarian cancer among American women are much lower than certain other cancers, the death-to-incidence ratio for ovarian cancer is considerably higher (Siegal et al., *C A Cancer J Clin* 66:7-30, 2016). Ovarian cancer is frequently diagnosed at an advanced stage, which contributes to its lethality. The current standard of care for ovarian cancer is surgery followed by chemotherapy, namely a combination of platinum agents and taxanes. Whilst the majority of patients respond to initial treatment, most experience a recurrence of the disease, resulting in a cycle of repeated surgeries and additional rounds of chemotherapy. Although recurrent ovarian cancers may respond to further treatment, virtually all of them will ultimately become resistant to currently available therapies. Despite recent advances in therapy such as PARP inhibitors for patients carrying BRCA or other homologous recombination deficiency (HRD) mutations, advanced ovarian cancer remains a disease of high unmet need.

Evidence suggests that ovarian cancer may be amenable to some forms of immunotherapy (Kandalaft et al., *J. Clin. Oncol.*, 29:925-933, 2011). For example, ovarian cancer patients whose tumors were positive for intraepithelial $CD8^+$ T lymphocyte infiltration had significantly better overall and progression-free survival than patients without intraepithelial $CD8^+$ T lymphocyte infiltration (Hamanishi et al., *PNAS*, 104:3360-65, 2007; and Zhang et al., *N. Engl. J. Med.*, 348:203-213, 2003). Moreover, some patients have shown spontaneous immune response to their tumors, demonstrated by detection of tumor-reactive T cells and antibodies in the blood, tumor or ascites of patients with advanced disease (Schliengar et al., *Clin Cancer Res*, 9:1517-1527, 2003). Blockade of the PD-1/PD-L1 checkpoint pathway has shown some benefit in ovarian cancer; PD-1 blockade monotherapy resulted in an overall response rate (ORR) of approximately 10-15% in early clinical trials (Hamanishi et al., supra). However, blockade of this pathway alone is clearly not sufficient.

In view of the high unmet need for effective therapies for ovarian cancer, it may be useful, as shown herein, to combine treatment with an agent to augment T-cell function (e.g., a PD-1 inhibitor such as an anti-PD-1 antibody) along with an agent against a target antigen (a bispecific anti-MUC16/anti-CD3 antibody).

BRIEF SUMMARY OF THE INVENTION

According to certain embodiments, the present invention provides methods for treating, ameliorating at least one symptom or indication, or inhibiting the growth of cancer in a subject. The methods according to this aspect of the invention comprise administering a therapeutically effective amount of an antibody or antigen-binding fragment thereof that specifically binds to programmed death 1 (PD-1) in combination with a therapeutically effective amount of a bispecific antibody that specifically binds to MUC16 and CD3 to a subject in need thereof.

In certain embodiments of the present invention, methods are provided for treating, ameliorating at least one symptom or indication, or inhibiting the growth of cancer in a subject. In certain embodiments of the present invention, methods are provided for delaying the growth of a tumor or preventing tumor recurrence. The methods, according to this and other aspects of the invention, comprise sequentially administering one or more doses of a therapeutically effective amount of an antibody or antigen-binding fragment thereof that specifically binds to PD-1 in combination with one or more doses of a therapeutically effective amount of a bispecific antibody that specifically binds to MUC16 and CD3 to a subject in need thereof.

In one aspect, the present invention provides a method of treating or inhibiting the growth of a tumor comprising administering to a subject in need thereof (a) a therapeutically effective amount of an antibody or antigen-binding fragment thereof that specifically binds programmed death 1 (PD-1); and (b) a therapeutically effective amount of a bispecific antibody comprising a first antigen-binding arm that specifically binds MUC16 and a second antigen-binding arm that specifically binds CD3. In some cases, the anti-PD-1 antibody is administered prior to, concurrent with or after the bispecific antibody. In some cases, the anti-PD-1 antibody is administered prior to the bispecific antibody. In some cases, the anti-PD-1 antibody is administered at least 1 week prior to the bispecific antibody. In some cases, one or more doses of the anti-PD-1 antibody are administered in combination with one or more doses of the bispecific antibody. In some cases, the anti-PD-1 antibody is administered at a dose of between 0.1 mg/kg and 20 mg/kg of the subject's body weight. In some cases, each dose of the anti-PD-1 antibody comprises between 10-8000 micrograms. In some cases, the bispecific antibody is administered at a dose of between 0.1 mg/kg and 20 mg/kg of the subject's body weight. In some cases, each dose of the bispecific antibody comprises between 10-8000 micrograms. In some cases, each dose of the anti-PD-1 antibody is administered 0.5-12 weeks after the immediately preceding dose. In some cases, each dose of the bispecific antibody is administered 0.5-12 weeks after the immediately preceding dose. In various embodiments, the antibodies are administered intravenously, subcutaneously, or intraperitoneally.

In some embodiments, the tumor comprises an ovarian cancer. In some embodiments, the subject is resistant or inadequately responsive to, or relapsed after, prior therapy.

In some cases, the method further comprises administering to the subject a third therapeutic agent or therapy. In some embodiments, the third therapeutic agent or therapy is selected from the group consisting of radiation, surgery, a chemotherapeutic agent, a cancer vaccine, a PD-L1 inhibitor, a LAG-3 inhibitor, a CTLA-4 inhibitor, a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an angiopoietin-2 (Ang2) inhibitor, a transforming growth factor beta (TGF.beta.) inhibitor, an epidermal growth factor receptor (EGFR) inhibitor, an antibody to a tumor-specific antigen, *Bacillus* Calmette-Guerin vaccine, granulocyte-macrophage colony-stimulating factor, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

In some embodiments, the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34. In some cases, HCDR1 comprises the amino acid sequence of SEQ ID NO: 35; HCDR2 comprises the amino acid sequence of SEQ ID NO: 36; HCDR3 comprises the amino acid sequence of SEQ ID NO: 37; LCDR1 comprises the amino acid sequence of SEQ ID NO: 38; LCDR2 comprises the amino acid sequence of SEQ ID NO: 39; and LCDR3 comprises the amino acid sequence of SEQ ID NO: 40. In some cases, the HCVR comprises the amino acid sequence of SEQ ID NO: 33, and the LCVR comprises the amino acid sequence of SEQ ID NO: 34. In some embodiments, the anti-PD-1 antibody comprises a heavy chain comprising the amino acid sequence of SEQ ID NO: 41, and a light chain comprising the amino acid sequence of SEQ ID NO: 42.

In some embodiments, the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2. In some cases, A-HCDR1 comprises the amino acid sequence of SEQ ID NO: 8; A-HCDR2 comprises the amino acid sequence of SEQ ID NO: 9; A-HCDR3 comprises the amino acid sequence of SEQ ID NO: 10; A-LCDR1 comprises the amino acid sequence of SEQ ID NO: 11; A-LCDR2 comprises the amino acid sequence of SEQ ID NO: 12; and A-LCDR3 comprises the amino acid sequence of SEQ ID NO: 13. In some cases, the A-HCVR comprises the amino acid sequence of SEQ ID NO:1 and the A-LCVR comprises the amino acid sequence of SEQ ID NO:2.

In some embodiments, the second antigen-binding arm of the bispecific antibody comprises three heavy chain CDRs (B-HCDR1, B-HCDR2 and B-HCDR3) of a heavy chain variable region (B-HCVR) comprising an amino acid sequence selected from the group consisting of SEQ ID NOs: 3, 4, 5, 6 and 7, and three light chain CDRs (B-LCDR1, B-LCDR2 and B-LCDR3) of a light chain variable region (B-LCVR) comprising the amino acid sequence of SEQ ID NO: 2. In some cases, B-HCDR1, B-HCDR2 and B-HCDR3 comprise, respectively, the amino acid sequences selected from the group consisting of SEQ ID NOs: 14-15-16, 17-18-19, 20-21-22, 23-24-25, and 26-27-28; and B-LCDR1, B-LCDR2 and B-LCDR3 comprise, respectively, the amino acid sequences of SEQ ID NOs: 11-12-13. In some cases, the B-HCVR comprises an amino acid sequence selected from the group consisting of SEQ ID NOs: 3, 4, 5, 6 and 7, and the B-LCVR comprises the amino acid sequence of SEQ ID NO: 2.

In some embodiments, the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2.

In some embodiments, the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 4, and three light chain CDRs (B-LCDR1, B-LCDR2 and B-LCDR3) of a light chain variable region (B-LCVR) comprising the amino acid sequence of SEQ ID NO: 2.

In some embodiments, the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 5, and three light chain CDRs (B-LCDR1, B-LCDR2 and B-LCDR3) of a light chain variable region (B-LCVR) comprising the amino acid sequence of SEQ ID NO: 2.

In some embodiments, the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 6, and three light chain CDRs (B-LCDR1, B-LCDR2 and B-LCDR3) of a light chain variable region (B-LCVR) comprising the amino acid sequence of SEQ ID NO: 2.

In some embodiments, the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2.

In some embodiments, the anti-PD-1 antibody, the bispecific antibody, or both, comprise a human IgG1 or IgG4 heavy chain constant region.

In another aspect, the present invention provides a method of treating or inhibiting the growth of a tumor comprising administering to a subject in need thereof (a) a therapeutically effective amount of an antibody or antigen-binding fragment thereof that specifically binds programmed death 1 (PD-1); and (b) a therapeutically effective amount of a bispecific antibody comprising a first antigen-binding arm that specifically binds MUC16 and a second antigen-binding arm that specifically binds CD3, wherein: (a) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (b) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (c) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2.

In some embodiments of the method, the anti-PD-1 antibody and the bispecific antibody, respectively include the following: (a) HCDR1 comprises the amino acid sequence of SEQ ID NO: 35; HCDR2 comprises the amino acid sequence of SEQ ID NO: 36; HCDR3 comprises the amino acid sequence of SEQ ID NO: 37; LCDR1 comprises the amino acid sequence of SEQ ID NO: 38; LCDR2 comprises the amino acid sequence of SEQ ID NO: 39; and LCDR3 comprises the amino acid sequence of SEQ ID NO: 40; (b) A-HCDR1 comprises the amino acid sequence of SEQ ID NO: 8; A-HCDR2 comprises the amino acid sequence of SEQ ID NO: 9; A-HCDR3 comprises the amino acid sequence of SEQ ID NO: 10; A-LCDR1 comprises the amino acid sequence of SEQ ID NO: 11; A-LCDR2 comprises the amino acid sequence of SEQ ID NO: 12; and A-LCDR3 comprises the amino acid sequence of SEQ ID NO: 13; and (c) B-HCDR1 comprises the amino acid sequence of SEQ ID NO: 14; B-HCDR2 comprises the amino acid sequence of SEQ ID NO: 15; B-HCDR3 comprises the amino acid sequence of SEQ ID NO: 16; B-LCDR1 comprises the amino acid sequence of SEQ ID NO: 11; B-LCDR2 comprises the amino acid sequence of SEQ ID NO: 12; and B-LCDR3 comprises the amino acid sequence of SEQ ID NO: 13.

In some embodiments of the method, that anti-PD-1 antibody and the bispecific antibody, respectively, include the following: (a) the HCVR comprises the amino acid sequence of SEQ ID NO: 33, and the LCVR comprises the amino acid sequence of SEQ ID NO: 34; (b) the A-HCVR comprises the amino acid sequence of SEQ ID NO:1 and the A-LCVR comprises the amino acid sequence of SEQ ID NO:2; and (c) the B-HCVR comprises the amino acid sequence of SEQ ID NO: 3, and the B-LCVR comprises the amino acid sequence of SEQ ID NO: 2.

In some embodiments of the method, the anti-PD-1 antibody comprises a heavy chain comprising the amino acid sequence of SEQ ID NO: 41, and a light chain comprising the amino acid sequence of SEQ ID NO: 42; the first antigen binding arm of the bispecific antibody comprises a heavy chain comprising the amino acid sequence of SEQ ID NO: 29, and a light chain comprising the amino acid sequence of SEQ ID NO: 30; and the second antigen binding arm of the bispecific antibody comprises a heavy chain comprising the amino acid sequence of SEQ ID NO: 31, and a light chain comprising the amino acid sequence of SEQ ID NO: 30.

In some embodiments of the method, the tumor comprises an ovarian cancer.

In another aspect, the present invention provides a method of treating or inhibiting the growth of a tumor comprising administering to a subject in need thereof (a) a therapeutically effective amount of an antibody or antigen-binding fragment thereof that specifically binds programmed death 1 (PD-1); and (b) a therapeutically effective amount of a bispecific antibody comprising a first antigen-binding arm that specifically binds MUC16 and a second antigen-binding arm that specifically binds CD3, wherein: (a) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (b) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (c) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2.

In some embodiments of the method, the anti-PD-1 antibody and the bispecific antibody, respectively include the following: (a) HCDR1 comprises the amino acid sequence of SEQ ID NO: 35; HCDR2 comprises the amino acid sequence of SEQ ID NO: 36; HCDR3 comprises the amino acid sequence of SEQ ID NO: 37; LCDR1 comprises the amino acid sequence of SEQ ID NO: 38; LCDR2 comprises the amino acid sequence of SEQ ID NO: 39; and LCDR3 comprises the amino acid sequence of SEQ ID NO: 40; (b) A-HCDR1 comprises the amino acid sequence of SEQ ID NO: 8; A-HCDR2 comprises the amino acid sequence of SEQ ID NO: 9; A-HCDR3 comprises the amino acid sequence of SEQ ID NO: 10; A-LCDR1 comprises the amino acid sequence of SEQ ID NO: 11; A-LCDR2 comprises the amino acid sequence of SEQ ID NO: 12; and A-LCDR3 comprises the amino acid sequence of SEQ ID NO: 13; and (c) B-HCDR1 comprises the amino acid sequence of SEQ ID NO: 26; B-HCDR2 comprises the amino acid sequence of SEQ ID NO: 27; B-HCDR3 comprises the amino acid sequence of SEQ ID NO: 28; B-LCDR1 comprises the amino acid sequence of SEQ ID NO: 11; B-LCDR2 comprises the amino acid sequence of SEQ ID NO: 12; and B-LCDR3 comprises the amino acid sequence of SEQ ID NO: 13.

In some embodiments of the method, the anti-PD-1 antibody and the bispecific antibody, respectively include the following: (a) the HCVR comprises the amino acid sequence of SEQ ID NO: 33, and the LCVR comprises the amino acid sequence of SEQ ID NO: 34; (b) the A-HCVR comprises the amino acid sequence of SEQ ID NO:1 and the A-LCVR comprises the amino acid sequence of SEQ ID NO:2; and (c) the B-HCVR comprises the amino acid sequence of SEQ ID NO: 7, and the B-LCVR comprises the amino acid sequence of SEQ ID NO: 2.

In some embodiments of the method, the anti-PD-1 antibody comprises a heavy chain comprising the amino acid sequence of SEQ ID NO: 41, and a light chain comprising the amino acid sequence of SEQ ID NO: 42; the first antigen binding arm of the bispecific antibody comprises a heavy chain comprising the amino acid sequence of SEQ ID NO: 29, and a light chain comprising the amino acid sequence of SEQ ID NO: 30; and the second antigen binding arm of the bispecific antibody comprises a heavy chain comprising the amino acid sequence of SEQ ID NO: 32, and a light chain comprising the amino acid sequence of SEQ ID NO: 30.

In some embodiments of the method, the tumor comprises an ovarian cancer.

In various embodiments of any one of the methods discussed above or herein, the anti-tumor activity of the bispecific antibody is not significantly impeded by circulating CA-125 at a concentration of up to 10 kU/ml. In various embodiments of any one of the methods discussed above or herein, the subject has been diagnosed with ovarian cancer, and the subject has circulating levels of CA-125 of up to 10 kU/ml. In some embodiments of the methods discussed above or herein, the subject has an elevated serum level of CA-125 prior to beginning treatment. In some embodiments of the methods discussed above or herein, the subject has a serum level of CA-125 greater than or equal to 2 times the upper limit of normal CA-125 serum levels prior to beginning treatment. Some embodiments of the methods discussed above or herein include monitoring serum levels of CA-125, e.g., to gauge the effectiveness of treatment by comparing serum levels of CA-125 at various points during or following treatment to a baseline level of serum CA-125 in a specific patient or a baseline level of serum CA-125 in an aggregate patient population.

In some embodiments, the antibodies discussed herein are used in the manufacture of a medicament for use in any of the methods discussed above or herein. In some embodiments, the antibodies discussed herein are for use in medicine or for use in the treatment of cancer as discussed above or herein. For example, the present disclosure includes:

(A) Use of a bispecific antibody comprising a first antigen-binding arm that specifically binds MUC16 and a second antigen-binding arm that specifically binds CD3 in the manufacture of a medicament for treating or inhibiting the growth of a tumor in a subject in need thereof in combination with an antibody or antigen-binding fragment thereof that specifically binds programmed death 1 (PD-1);

(B) Use of an antibody or antigen-binding fragment thereof that specifically binds programmed death 1 (PD-1) in the manufacture of a medicament for treating or inhibiting the growth of a tumor in a subject in need thereof in combination with a bispecific antibody comprising a first antigen-binding arm that specifically binds MUC16 and a second antigen-binding arm that specifically binds CD3;

(C) Use of a bispecific antibody comprising a first antigen-binding arm that specifically binds MUC16 and a second antigen-binding arm that specifically binds CD3 in the manufacture of a medicament for treating or inhibiting the growth of a tumor in a subject in need thereof in combination with an antibody or antigen-binding fragment thereof that specifically binds programmed death 1 (PD-1), wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2;

(D) Use of an antibody or antigen-binding fragment thereof that specifically binds programmed death 1 (PD-1) in the manufacture of a medicament for treating or inhibiting the growth of a tumor in a subject in need thereof in combination with a bispecific antibody comprising a first antigen-binding arm that specifically binds MUC16 and a second antigen-binding arm that specifically binds CD3, wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2;

(E) Use of a bispecific antibody comprising a first antigen-binding arm that specifically binds MUC16 and a second antigen-binding arm that specifically binds CD3 in the manufacture of a medicament for treating or inhibiting the growth of a tumor in a subject in need thereof in combination with an antibody or antigen-binding fragment thereof that specifically binds programmed death 1 (PD-1), wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2;

(F) Use of an antibody or antigen-binding fragment thereof that specifically binds programmed death 1 (PD-1) in the manufacture of a medicament for treating or inhibiting the growth of a tumor in a subject in need thereof in combination with a bispecific antibody comprising a first antigen-binding arm that specifically binds MUC16 and a second antigen-binding arm that specifically binds CD3, wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2;

(G) A bispecific antibody comprising a first antigen-binding arm that specifically binds MUC16 and a second antigen-binding arm that specifically binds CD3 for use in treating or inhibiting the growth of a tumor in a subject in need thereof in combination with an antibody or antigen-binding fragment thereof that specifically binds programmed death 1 (PD-1);

(H) An antibody or antigen-binding fragment thereof that specifically binds programmed death 1 (PD-1) for use in treating or inhibiting the growth of a tumor in a subject in need thereof in combination with a bispecific antibody comprising a first antigen-binding arm that specifically binds MUC16 and a second antigen-binding arm that specifically binds CD3;

(I) A bispecific antibody comprising a first antigen-binding arm that specifically binds MUC16 and a second antigen-binding arm that specifically binds CD3 for use in treating or inhibiting the growth of a tumor in a subject in need thereof in combination with an antibody or antigen-binding fragment thereof that specifically binds programmed death 1 (PD-1), wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2;

(J) An antibody or antigen-binding fragment thereof that specifically binds programmed death 1 (PD-1) for use in treating or inhibiting the growth of a tumor in a subject in need thereof in combination with a bispecific antibody comprising a first antigen-binding arm that specifically binds MUC16 and a second antigen-binding arm that specifically binds CD3, wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2;

(K) A bispecific antibody comprising a first antigen-binding arm that specifically binds MUC16 and a second antigen-binding arm that specifically binds CD3 for use in treating or inhibiting the growth of a tumor in a subject in need thereof in combination with an antibody or antigen-binding fragment thereof that specifically binds programmed death 1 (PD-1), wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2; and (L) An antibody or antigen-binding fragment thereof that specifically binds programmed death 1 (PD-1) for use in treating or inhibiting the growth of a tumor in a subject in need thereof in combination with a bispecific antibody comprising a first antigen-binding arm that specifically binds MUC16 and a second antigen-binding arm that specifically binds CD3, wherein: (i) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34; (ii) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (iii) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2.

Other embodiments of the present invention will become apparent from a review of the ensuing detailed description.

DETAILED DESCRIPTION

Figure 1:
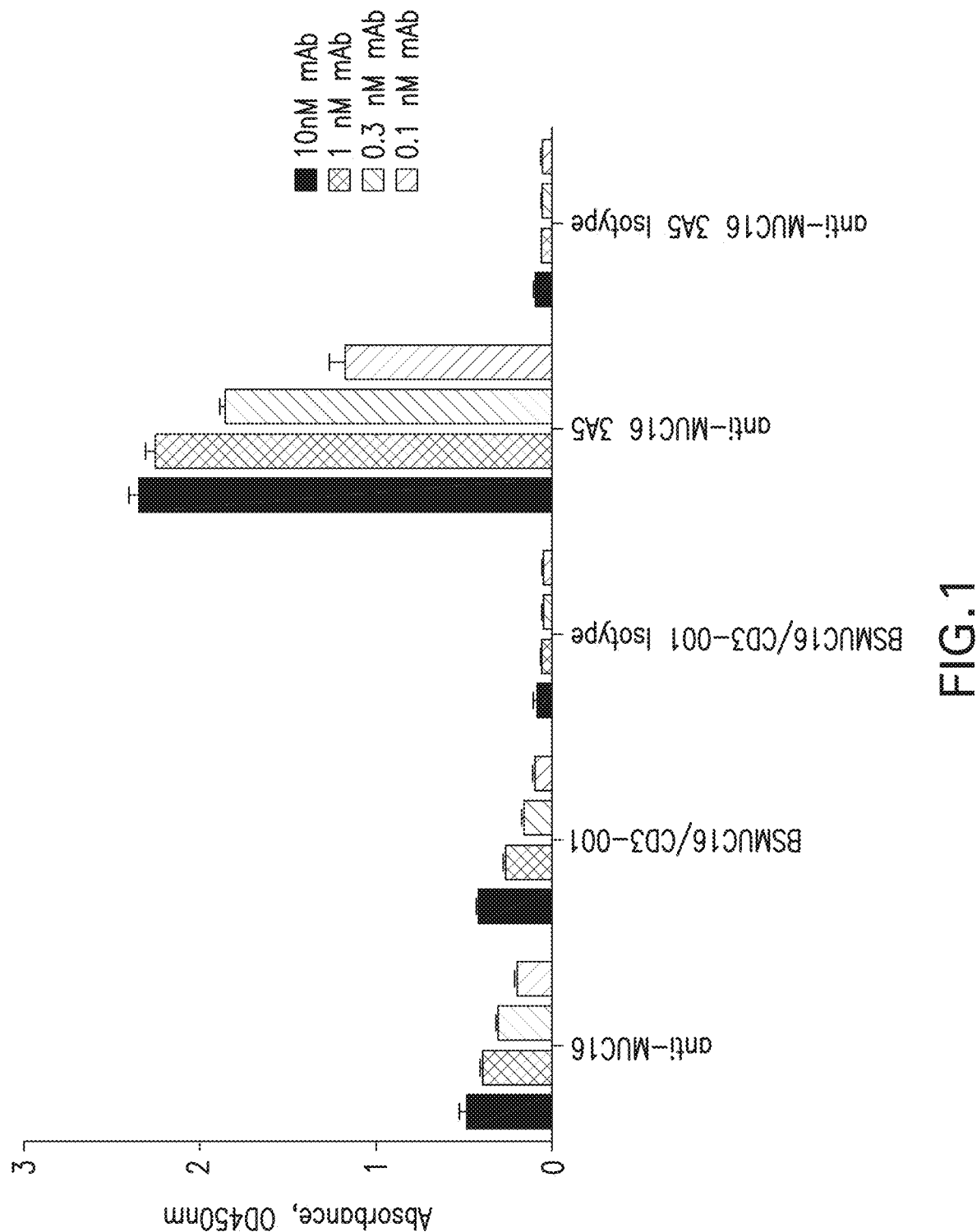
FIG. 1 illustrates the binding of various concentrations of anti-MUC16 clone 3A5 and BSMUC16/CD3-001 to CA125, as determined by ELISA (described in Example 2 herein). BSMUC16/CD3-001 and its MUC16 parental antibody displayed a markedly reduced binding signal at all concentrations tested in comparison to an anti-MUC16 clone 3A5 that binds to the repeat region of MUC16.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention. Any specific value discussed above or herein may be combined with another related value discussed above or herein to recite a range with the values representing the upper and lower ends of the range, and such ranges are encompassed within the scope of the present disclosure.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Methods for Treating or Inhibiting the Growth of Cancers

The present invention includes methods for treating, ameliorating or reducing the severity of at least one symptom or indication, or inhibiting the growth of a cancer in a subject. The methods according to this aspect of the invention comprise administering a therapeutically effective amount of an antibody or antigen-binding fragment thereof that specifically binds PD-1 in combination with a therapeutically effective amount of a bispecific antibody against MUC16 and CD3 to a subject in need thereof. As used herein, the terms "treat", "treating", or the like, mean to alleviate symptoms, eliminate the causation of symptoms either on a temporary or permanent basis, to delay or inhibit tumor growth, to reduce tumor cell load or tumor burden, to promote tumor regression, to cause tumor shrinkage, necrosis and/or disappearance, to prevent tumor recurrence, and/or to increase duration of survival of the subject.

As used herein, the expression "a subject in need thereof" means a human or non-human mammal that exhibits one or more symptoms or indications of cancer, and/or who has been diagnosed with cancer, including an ovarian cancer and who needs treatment for the same. In many embodiments, the term "subject" may be interchangeably used with the term "patient". For example, a human subject may be diagnosed with a primary or a metastatic tumor and/or with one or more symptoms or indications including, but not limited to, enlarged lymph node(s), swollen abdomen, chest pain/pressure, unexplained weight loss, fever, night sweats, persistent fatigue, loss of appetite, enlargement of spleen, itching. The expression includes subjects with primary or established ovarian tumors. In specific embodiments, the expression includes human subjects that have and need treatment for ovarian cancer or another tumor expressing MUC16. In other specific embodiments, the expression includes subjects with MUC16+ tumors (e.g., a tumor with MUC16 expression as determined by flow cytometry). In certain embodiments, the expression "a subject in need thereof" includes patients with an ovarian cancer that is resistant to or refractory to or is inadequately controlled by prior therapy (e.g., treatment with a conventional anti-cancer agent). For example, the expression includes subjects who have been treated with chemotherapy, such as a platinum-based chemotherapeutic agent (e.g., cisplatin) or a taxol compound (e.g., docetaxel). The expression also includes subjects with an ovarian tumor for which conventional anti-cancer therapy is inadvisable, for example, due to toxic side effects. For example, the expression includes patients who have received one or more cycles of chemotherapy with toxic side effects. In certain embodiments, the expression "a subject in need thereof" includes patients with an ovarian tumor which has been treated but which has subsequently relapsed or metastasized. For example, patients with an ovarian tumor that may have received treatment with one or more anti-cancer agents leading to tumor regression; however, subsequently have relapsed with cancer resistant to the one or more anti-cancer agents (e.g., chemotherapy-resistant cancer) are treated with the methods of the present invention.

The expression "a subject in need thereof" also includes subjects who are at risk of developing ovarian cancer, e.g., persons with a family history of ovarian cancer, persons with a past history of infections associated with ovarian cancer, persons with mutations in the BRCA1/2 genes, or persons with an immune system compromised due to HIV infection or due to immunosuppressive medications.

In certain embodiments, the methods of the present invention may be used to treat patients that show elevated levels of one or more cancer-associated biomarkers (e.g., programmed death ligand 1 (PD-L1), CA125, human epididymis protein 4 (HE4), and/or carcinoembryonic antigen (CEA)). For example, the methods of the present invention comprise administering a therapeutically effective amount of an anti-PD-1 antibody in combination with a bispecific anti-MUC16/anti-CD3 antibody to a patient with an elevated level of PD-L1 and/or CA125.

In certain embodiments, the methods of the present invention are used in a subject with an ovarian cancer. The terms "tumor", "cancer" and "malignancy" are interchangeably used herein. The term "ovarian cancer", as used herein, refers to tumors of the ovary and fallopian tube, and includes serous cancer, endometrioid carcinoma, clear cell carcinoma, and mucinous carcinoma.

According to certain embodiments, the present invention includes methods for treating, or delaying or inhibiting the growth of a tumor. In certain embodiments, the present invention includes methods to promote tumor regression. In certain embodiments, the present invention includes methods to reduce tumor cell load or to reduce tumor burden. In certain embodiments, the present invention includes methods to prevent tumor recurrence. The methods, according to this aspect of the invention, comprise sequentially administering a therapeutically effective amount of an anti-PD-1 antibody in combination with a bispecific anti-MUC16/anti-CD3 antibody to a subject in need thereof, wherein each antibody is administered to the subject in multiple doses, e.g., as part of a specific therapeutic dosing regimen. For example, the therapeutic dosing regimen may comprise administering one or more doses of an anti-PD-1 antibody to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the one or more doses of anti-PD-1 antibody are administered in combination with one or more doses of a therapeutically effective amount of a bispecific anti-MUC16/anti-CD3 antibody, wherein the one or more doses of the bispecific antibody are administered to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

In certain embodiments, each dose of the anti-MUC16/anti-CD3 antibody is administered in more than 1 fractions, e.g., in 2-5 fractions ("split dosing") within the given dosing period. The anti-MUC16/anti-CD3 bispecific antibody may be administered in split doses to reduce or eliminate the cytokine "spikes" induced in response to administration of the antibody. Cytokine spikes refer to the clinical symptoms of the cytokine release syndrome ("cytokine storm") and infusion related reactions. In certain embodiments, the methods of the present invention comprise administering one or more doses of anti-PD-1 antibody in combination with one or more doses of a bispecific anti-MUC16/anti-CD3 antibody to a subject in need thereof, wherein a dose of the bispecific antibody is administered as split doses, or in more than 1 fractions, e.g., as 2 fractions, as 3 fractions, as 4 fractions or as 5 fractions within the given dosing period. In certain embodiments, a dose of the bispecific antibody is split into 2 or more fractions, wherein each fraction comprises an amount of the antibody equal to the other fractions.

For example, a dose of anti-MUC16/anti-CD3 antibody comprising 1000 micrograms may be administered once a week, wherein the dose is administered in 2 fractions within the week, each fraction comprising 500 micrograms. In certain embodiments, a dose of the bispecific antibody is administered split into 2 or more fractions, wherein the fractions comprise unequal amounts of the antibody, e.g., more than or less than the first fraction. For example, a dose of anti-MUC16/anti-CD3 antibody comprising 1000 micrograms may be administered once a week, wherein the dose is administered in 2 fractions within the week, wherein the first fraction comprises 700 micrograms and the second fraction comprises 300 micrograms. As another example, a dose of anti-MUC16/anti-CD3 antibody comprising 1000 micrograms may be administered once in 2 weeks, wherein the dose is administered in 3 fractions within the 2-week period, wherein the first fraction comprises 400 micrograms, the second fraction comprises 300 micrograms and the third fraction comprises 300 micrograms.

In certain embodiments, the present invention includes methods to inhibit, retard or stop tumor metastasis or tumor infiltration into peripheral organs. The methods, according to this aspect, comprise administering a therapeutically effective amount of an anti-PD-1 antibody to a subject in need thereof in combination with a bispecific anti-MUC16/anti-CD3 antibody.

In specific embodiments, the present invention provides methods for increased anti-tumor efficacy or increased tumor inhibition. The methods, according to this aspect of the invention, comprise administering to a subject with an ovarian cancer a therapeutically effective amount of an anti-PD-1 antibody prior to administering a therapeutically effective amount of a bispecific anti-MUC16/anti-CD3 antibody, wherein the anti-PD-1 antibody may be administered about 1 day, more than 1 day, more than 2 days, more than 3 days, more than 4 days, more than 5 days, more than 6 days, more than 7 days, or more than 8 days prior to the bispecific antibody. In certain embodiments, the methods provide for increased tumor inhibition, e.g., by about 20%, more than 20%, more than 30%, more than 40% more than 50%, more than 60%, more than 70% or more than 80% as compared to a subject administered with the bispecific antibody prior to the anti-PD-1 antibody.

In certain embodiments, the methods of the present invention comprise administering a therapeutically effective amount of an anti-PD-1 antibody and a therapeutically effective amount of a bispecific anti-CD3×MUC16 antibody to a subject with an ovarian cancer. In specific embodiments, the ovarian cancer is serous cancer. In further embodiments, the ovarian cancer is indolent or aggressive. In certain embodiments, the subject is not responsive to prior therapy or has relapsed after prior therapy. In certain embodiments, the methods of the present invention further comprise administering an additional therapeutic agent to the subject.

In certain embodiments, the methods of the present invention comprise administering a therapeutically effective amount of a bispecific anti-MUC16/anti-CD3 antibody to a subject with a MUC16+ cancer. In specific embodiments, the cancer is an ovarian cancer. In further embodiments, the ovarian cancer is indolent or aggressive. In some embodiments, the cancer is a platinum-resistant ovarian cancer. In some embodiments, the cancer is a taxol-resistant ovarian cancer. In some embodiments, the cancer is fallopian tube cancer. In some embodiments, the cancer is primary peritoneal cancer, optionally in which the patient has elevated levels of serum CA-125. In specific embodiments, the cancer is pancreatic cancer (e.g., pancreatic adenocarcinoma). In certain embodiments, the subject is not responsive to prior therapy or has relapsed after prior therapy (e.g., chemotherapy).

In certain embodiments, the methods of the present invention comprise administering an anti-PD-1 antibody in combination with a bispecific anti-MUC16/anti-CD3 antibody to a subject in need thereof as a "first line" treatment (e.g., initial treatment). In other embodiments, an anti-PD-1 antibody in combination with a bispecific anti-MUC16/anti-CD3 antibody is administered as a "second line" treatment (e.g., after prior therapy). For example, an anti-PD-1 antibody in combination with a bispecific anti-MUC16/anti-CD3 antibody is administered as a "second line" treatment to a subject that has relapsed after prior therapy with, e.g., chemotherapy.

In certain embodiments, the methods of the present invention are used to treat a patient with a MRD-positive disease. Minimum residual disease (MRD) refers to small numbers of cancer cells that remain in the patient during or after treatment, wherein the patient may or may not show symptoms or signs of the disease. Such residual cancer cells, if not eliminated, frequently lead to relapse of the disease. The present invention includes methods to inhibit and/or eliminate residual cancer cells in a patient upon MRD testing. MRD may be assayed according to methods known in the art (e.g., MRD flow cytometry). The methods, according to this aspect of the invention, comprise administering an anti-PD-1 antibody in combination with a bispecific anti-MUC16/anti-CD3 antibody to a subject in need thereof.

The methods of the present invention, according to certain embodiments, comprise administering to a subject a therapeutically effective amount of each of an anti-PD-1 antibody and a bispecific anti-MUC16/anti-CD3 antibody in combination with a third therapeutic agent. The third therapeutic agent may be an agent selected from the group consisting of, e.g., radiation, chemotherapy, surgery, a cancer vaccine, a PD-L1 inhibitor (e.g., an anti-PD-L1 antibody), a LAG3 inhibitor (e.g., an anti-LAG3 antibody), a CTLA-4 inhibitor (e.g., an anti-CTLA-4 antibody), a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an Ang2 inhibitor, a transforming growth factor beta (TGF.beta.) inhibitor, an epidermal growth factor receptor (EGFR) inhibitor, an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin), granulocyte-macrophage colony-stimulating factor, a cytotoxin, a chemotherapeutic agent, an IL-6R inhibitor, an IL-4R inhibitor, an IL-10 inhibitor, a cytokine such as IL-2, IL-7, IL-21, and IL-15, an anti-inflammatory drug such as corticosteroids, and non-steroidal anti-inflammatory drugs, and a dietary supplement such as anti-oxidants. In certain embodiments, the antibodies may be administered in combination with therapy including a chemotherapeutic agent (e.g., paclitaxel, carboplatin, doxorubicin, cyclophosphamide, cisplatin, gemcitabine or docetaxel), radiation and surgery. As used herein, the phrase "in combination with" means that the antibodies are administered to the subject at the same time as, just before, or just after administration of the third therapeutic agent. In certain embodiments, the third therapeutic agent is administered as a co-formulation with the antibodies. In a related embodiment, the present invention includes methods comprising administering a therapeutically effective amount of an anti-PD-1 antibody in combination with a bispecific anti- MUC16/anti-CD3 antibody to a subject who is on a background anti-cancer therapeutic regimen. The background anti-cancer therapeutic regimen may comprise a course of administration of, e.g., a chemotherapeutic agent, or radiation. The anti-PD-1 antibody in combination with a bispecific anti-MUC16/anti-CD3 antibody may be added on top of the background anti-cancer therapeutic regimen. In some embodiments, the antibodies are added as part of a "background step-down" scheme, wherein the background anti-cancer therapy is gradually withdrawn from the subject over time (e.g., in a stepwise fashion) while the antibodies are administered to the subject at a constant dose, or at an increasing dose, or at a decreasing dose, over time.

In certain embodiments, the methods of the present invention comprise administering to a subject in need thereof a therapeutically effective amount of an anti-PD-1 antibody in combination with a therapeutically effective amount of a bispecific anti-MUC16/anti-CD3 antibody, wherein administration of the antibodies leads to increased inhibition of tumor growth. In certain embodiments, tumor growth is inhibited by at least about 10%, about 20%, about 30%, about 40%, about 50%, about 60%, about 70% or about 80% as compared to an untreated subject or a subject administered with either antibody as monotherapy. In certain embodiments, the administration of an anti-PD-1 antibody and a bispecific anti-MUC16/anti-CD3 antibody leads to increased tumor regression, tumor shrinkage and/or disappearance. In certain embodiments, the administration of an anti-PD-1 antibody and a bispecific anti-MUC16/anti-CD3 antibody leads to delay in tumor growth and development, e.g., tumor growth may be delayed by about 3 days, more than 3 days, about 7 days, more than 7 days, more than 15 days, more than 1 month, more than 3 months, more than 6 months, more than 1 year, more than 2 years, or more than 3 years as compared to an untreated subject or a subject treated with either antibody as monotherapy. In certain embodiments, administration of an anti-PD-1 antibody in combination with a bispecific anti-MUC16/anti-CD3 antibody prevents tumor recurrence and/or increases duration of survival of the subject, e.g., increases duration of survival by more than 15 days, more than 1 month, more than 3 months, more than 6 months, more than 12 months, more than 18 months, more than 24 months, more than 36 months, or more than 48 months than an untreated subject or a subject which is administered either antibody as monotherapy. In certain embodiments, administration of the antibodies in combination increases progression-free survival or overall survival. In certain embodiments, administration of an anti-PD-1 antibody in combination with a bispecific anti-MUC16/anti-CD3 antibody increases response and duration of response in a subject, e.g., by more than 2%, more than 3%, more than 4%, more than 5%, more than 6%, more than 7%, more than 8%, more than 9%, more than 10%, more than 20%, more than 30%, more than 40% or more than 50% over an untreated subject or a subject which has received either antibody as monotherapy. In certain embodiments, administration of an anti-PD-1 antibody and a bispecific anti-MUC16/anti-CD3 antibody to a subject with an ovarian cancer leads to complete disappearance of all evidence of tumor cells ("complete response"). In certain embodiments, administration of an anti-PD-1 antibody and a bispecific anti-MUC16/anti-CD3 antibody to a subject with an ovarian cancer leads to at least 30% or more decrease in tumor cells or tumor size ("partial response"). In certain embodiments, administration of an anti-PD-1 antibody and a bispecific anti-MUC16/anti-CD3 antibody to a subject with an ovarian cancer leads to complete or partial disappearance of tumor cells/lesions including new measurable lesions. Tumor reduction can be measured by any of the methods known in the art, e.g., X-rays, positron emission tomography (PET), computed tomography (CT), magnetic resonance imaging (MRI), cytology, histology, or molecular genetic analyses. In certain embodiments, administration of an anti-PD-1 antibody and a bispecific anti-MUC16/anti-CD3 antibody produces a synergistic anti-tumor effect that exceeds the combined effects of the two agents when administered alone.

In certain embodiments, the combination of administered antibodies is safe and well-tolerated by a patient wherein there is no increase in an adverse side effect (e.g., increased cytokine release ("cytokine storm") or increased T-cell activation) as compared to a patient administered with the bispecific antibody as monotherapy.

Anti-PD-1 Antibodies and Antigen-Binding Fragments Thereof

According to certain exemplary embodiments of the present invention, the methods comprise administering a therapeutically effective amount of an anti-PD-1 antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (X) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for PD-1 or a fragment thereof, and the other arm of the immunoglobulin is specific for a second therapeutic target or is conjugated to a therapeutic moiety.

Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab.sup.2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J. Am. Chem. Soc. [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind PD-1. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PD-1, as used in the context of the present invention, includes antibodies that bind PD-1 or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PD-1 may, however, have cross-reactivity to other antigens, such as PD-1 molecules from other (non-human) species.

According to certain exemplary embodiments of the present invention, the anti-PD-1 antibody, or antigen-binding fragment thereof comprises a heavy chain variable region (HCVR), light chain variable region (LCVR), and/or complementarity determining regions (CDRs) comprising any of the amino acid sequences of the anti-PD-1 antibodies as set forth in US Patent Publication No. 20150203579. In certain exemplary embodiments, the anti-PD-1 antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 33 and the light chain complementarity determining regions (LCDRs) of a light chain variable region (LCVR) comprising the amino acid sequence of SEQ ID NO: 34. According to certain embodiments, the anti-PD-1 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 35; the HCDR2 comprises the amino acid sequence of SEQ ID NO: 36; the HCDR3 comprises the amino acid sequence of SEQ ID NO: 37; the LCDR1 comprises the amino acid sequence of SEQ ID NO: 38; the LCDR2 comprises the amino acid sequence of SEQ ID NO: 39; and the LCDR3 comprises the amino acid sequence of SEQ ID NO: 40. In yet other embodiments, the anti-PD-1 antibody or antigen-binding fragment thereof comprises an HCVR comprising SEQ ID NO: 33 and an LCVR comprising SEQ ID NO: 34. In certain embodiments, the methods of the present invention comprise the use of an anti-PD-1 antibody, wherein the antibody comprises a heavy chain comprising the amino acid sequence of SEQ ID NO: 41. In some embodiments, the anti-PD-1 antibody comprises a light chain comprising the amino acid sequence of SEQ ID NO: 42. An exemplary antibody comprising a heavy chain comprising the amino acid sequence of SEQ ID NO: 41 and a light chain comprising the amino acid sequence of SEQ ID NO: 42 is the fully human anti-PD-1 antibody known as REGN2810 (also known as cemiplimab). According to certain exemplary embodiments, the methods of the present invention comprise the use of REGN2810, or a bioequivalent thereof. The term "bioequivalent", as used herein, refers to anti-PD-1 antibodies or PD-1-binding proteins or fragments thereof that are pharmaceutical equivalents or pharmaceutical alternatives whose rate and/or extent of absorption do not show a significant difference with that of REGN2810 when administered at the same molar dose under similar experimental conditions, either single dose or multiple dose. In the context of the invention, the term refers to antigen-binding proteins that bind to PD-1 which do not have clinically meaningful differences with REGN2810 in their safety, purity and/or potency.

Other anti-PD-1 antibodies that can be used in the context of the methods of the present invention include, e.g., the antibodies referred to and known in the art as nivolumab (U.S. Pat. No. 8,008,449), pembrolizumab (U.S. Pat. No. 8,354,509), MEDI0608 (U.S. Pat. No. 8,609,089), pidilizumab (U.S. Pat. No. 8,686,119), or any of the anti-PD-1 antibodies as set forth in U.S. Pat. No. 6,808,710, 7,488,802, 8,168,757, 8,354,509, 8,779,105, or 8,900,587.

The anti-PD-1 antibodies used in the context of the methods of the present invention may have pH-dependent binding characteristics. For example, an anti-PD-1 antibody for use in the methods of the present invention may exhibit reduced binding to PD-1 at acidic pH as compared to neutral pH. Alternatively, an anti-PD-1 antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to PD-1 at acidic pH as compared to neutral pH" is expressed in terms of a ratio of the $K_D$ value of the antibody binding to PD-1 at acidic pH to the $K_D$ value of the antibody binding to PD-1 at neutral pH (or vice versa). For example, an antibody or antigen-binding fragment thereof may be regarded as exhibiting "reduced binding to PD-1 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Bispecific Anti-MUC16/Anti-CD3 Antibodies

According to certain exemplary embodiments of the present invention, the methods comprise administering a therapeutically effective amount of a bispecific antibody that specifically binds CD3 and MUC16. Such antibodies may be referred to herein as, e.g., "anti-MUC16/anti-CD3," or "anti-MUC16×CD3" or "MUC16×CD3" bispecific antibodies, or other similar terminology.

As used herein, the expression "bispecific antibody" refers to an immunoglobulin protein comprising at least a first antigen-binding domain and a second antigen-binding domain. In the context of the present invention, the first antigen-binding domain specifically binds a first antigen (e.g., MUC16), and the second antigen-binding domain specifically binds a second, distinct antigen (e.g., CD3). Each antigen-binding domain of a bispecific antibody comprises a heavy chain variable domain (HCVR) and a light chain variable domain (LCVR), each comprising three CDRs. In the context of a bispecific antibody, the CDRs of the first antigen-binding domain may be designated with the prefix "A" and the CDRs of the second antigen-binding domain may be designated with the prefix "B". Thus, the CDRs of the first antigen-binding domain may be referred to herein as A-HCDR1, A-HCDR2, and A-HCDR3; and the CDRs of the second antigen-binding domain may be referred to herein as B-HCDR1, B-HCDR2, and B-HCDR3.

The first antigen-binding domain and the second antigen-binding domain are each connected to a separate multimerizing domain. As used herein, a "multimerizing domain" is any macromolecule, protein, polypeptide, peptide, or amino acid that has the ability to associate with a second multimerizing domain of the same or similar structure or constitution. In the context of the present invention, the multimerizing component is an Fc portion of an immunoglobulin (comprising a $C_{H2}$-$C_{H3}$ domain), e.g., an Fc domain of an IgG selected from the isotypes IgG1, IgG2, IgG3, and IgG4, as well as any allotype within each isotype group.

Bispecific antibodies of the present invention typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$_2$ bispecific formats (see, e.g., Klein et al. 2012, mAbs 4:6, 1-11, and references cited therein, for a review of the foregoing formats).

In the context of bispecific antibodies of the present invention, Fc domains may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_{H2}$ or a $C_{H3}$ region, wherein the modification increases the affinity of the Fc domain to FcRn in an acidic environment (e.g., in an endosome where pH ranges from about 5.5 to about 6.0). Non-limiting examples of such Fc modifications are disclosed in US Patent Publication No. 20150266966, incorporated herein in its entirety.

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). See, for example, U.S. Pat. No. 8,586,713. Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in US Patent Publication No. 20140243504, which is herein incorporated in its entirety. Chimeric Fc domains having these general structural arrangements, and variants thereof, can have altered Fc receptor binding, which in turn affects Fc effector function.

According to certain exemplary embodiments of the present invention, the bispecific anti-MUC16/anti-CD3 antibody, or antigen-binding fragment thereof comprises heavy chain variable regions (A-HCVR and B-HCVR), light chain variable regions (A-LCVR and B-LCVR), and/or complementarity determining regions (CDRs) comprising any of the amino acid sequences of the bispecific anti-MUC16/anti-CD3 antibodies as set forth in US Patent Publication No. 20180112001. In certain exemplary embodiments, the bispecific anti-MUC16/anti-CD3 antibody or antigen-binding fragment thereof that can be used in the context of the methods of the present invention comprises: (a) a first antigen-binding arm comprising the heavy chain complementarity determining regions (A-HCDR1, A-HCDR2 and A-HCDR3) of a heavy chain variable region (A-HCVR) comprising the amino acid sequence of SEQ ID NO: 1 and the light chain complementarity determining regions (A-LCDR1, A-LCDR2 and A-LCDR3) of a light chain variable region (A-LCVR) comprising the amino acid sequence of SEQ ID NO: 2; and (b) a second antigen-binding arm comprising the heavy chain CDRs (B-HCDR1, B-HCDR2 and B-HCDR3) of a HCVR (B-HCVR) comprising an amino acid sequence of SEQ ID NO: 3, SEQ ID NO: 4, SEQ ID NO: 5, SEQ ID NO: 6 or SEQ ID NO: 7, and the light chain CDRs (B-LCDR1, B-LCDR2 and B-LCDR3) of a LCVR (B-LCVR) comprising the amino acid sequence of SEQ ID NO: 2. According to certain embodiments, the A-HCDR1 comprises the amino acid sequence of SEQ ID NO: 8; the A-HCDR2 comprises the amino acid sequence of SEQ ID NO: 9; the A-HCDR3 comprises the amino acid sequence of SEQ ID NO: 10; the A-LCDR1 comprises the amino acid sequence of SEQ ID NO: 11; the A-LCDR2 comprises the amino acid sequence of SEQ ID NO: 12; the A-LCDR3 comprises the amino acid sequence of SEQ ID NO: 13; the B-HCDR1 comprises the amino acid sequence of SEQ ID NO: 14, SEQ ID NO: 17, SEQ ID NO: 20, SEQ ID NO: 23, or SEQ ID NO: 26; the B-HCDR2 comprises the amino acid sequence of SEQ ID NO: 15, SEQ ID NO: 18, SEQ ID NO: 21, SEQ ID NO: 24, or SEQ ID NO: 27; and the B-HCDR3 comprises the amino acid sequence of SEQ ID NO: 16, SEQ ID NO: 19, SEQ ID NO: 22, SEQ ID NO: 25, or SEQ ID NO: 28; and the B-LCDR1 comprises the amino acid sequence of SEQ ID NO: 11; the B-LCDR2 comprises the amino acid sequence of SEQ ID NO: 12; the B-LCDR3 comprises the amino acid sequence of SEQ ID NO: 13. In yet other embodiments, the bispecific anti-MUC16/anti-CD3 antibody or antigen-binding fragment thereof comprises: (a) a first antigen-binding arm comprising a HCVR (A-HCVR) comprising SEQ ID NO: 1 and a LCVR (A-LCVR) comprising SEQ ID NO: 2; and (b) a second antigen-binding arm comprising a HCVR (B-HCVR) comprising SEQ ID NO: 3, SEQ ID NO: 4, SEQ ID NO: 5, SEQ ID NO: 6, or SEQ ID NO: 7, and a LCVR (B-LCVR) comprising SEQ ID NO: 2. In certain exemplary embodiments, the bispecific anti-CD3×MUC16 antibody comprises a MUC16-binding arm comprising a heavy chain comprising the amino acid sequence of SEQ ID NO: 29 and a light chain comprising the amino acid sequence of SEQ ID NO: 30, and a CD3-binding arm comprising a heavy chain comprising the amino acid sequence of SEQ ID NO: 31 and a light chain comprising the amino acid sequence of SEQ ID NO: 30. In certain exemplary embodiments, the bispecific anti-CD3×MUC16 antibody comprises a MUC16-binding arm comprising a heavy chain comprising the amino acid sequence of SEQ ID NO: 29 and a light chain comprising the amino acid sequence of SEQ ID NO: 30, and a CD3-binding arm comprising a heavy chain comprising the amino acid sequence of SEQ ID NO: 32 and a light chain comprising the amino acid sequence of SEQ ID NO: 30.

In certain embodiments, the anti-tumor activity of the bispecific anti-CD3×MUC16 antibodies of the present invention is not substantially impeded by the presence of high levels (e.g., up to 10,000 U/ml) of circulating CA125. Serum levels of CA125 are increased in the serum of the majority of ovarian cancer patients (median published levels are about 656 U/ml). As demonstrated in Example 2, below, high levels of CA125 in serum or ascites will not significantly interfere with the anti-tumor profile of the bispecific antibodies of the present invention.

Other bispecific anti-MUC16/anti-CD3 antibodies that can be used in the context of the methods of the present invention include, e.g., any of the antibodies as set forth in US Patent Publication No. 20180112001.

Combination Therapies

The methods of the present invention, according to certain embodiments, comprise administering to the subject an anti-MUC16/anti-CD3 bispecific antibody in combination with an anti-PD-1 antibody. In certain embodiments, the methods of the present invention comprise administering the antibodies for additive or synergistic activity to treat cancer, preferably an ovarian cancer. As used herein, the expression "in combination with" means that the anti-MUC16/anti-CD3 bispecific antibody is administered before, after, or concurrent with the anti-PD-1 antibody. The term "in combination with" also includes sequential or concomitant administration of anti-PD-1 antibody and a bispecific anti-MUC16/anti-CD3 antibody. For example, when administered "before" the bispecific anti-MUC16/anti-CD3 antibody, the anti-PD-1 antibody may be administered more than 150 hours, about 150 hours, about 100 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the bispecific anti-MUC16/anti-CD3 antibody. When administered "after" the bispecific anti-MUC16/anti-CD3 antibody, the anti-PD-1 antibody may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the bispecific anti-MUC16/anti-CD3 antibody. Administration "concurrent" with the bispecific anti-MUC16/anti-CD3 antibody means that the anti-PD-1 antibody is administered to the subject in a separate dosage form within less than 5 minutes (before, after, or at the same time) of administration of the bispecific anti-MUC16/anti-CD3 antibody, or administered to the subject as a single combined dosage formulation comprising both the anti-PD-1 antibody and the bispecific anti-MUC16/anti-CD3 antibody.

In certain embodiments, the methods of the present invention comprise administration of a third therapeutic agent wherein the third therapeutic agent is an anti-cancer drug. As used herein, "anti-cancer drug" means any agent useful to treat cancer including, but not limited to, cytotoxins and agents such as antimetabolites, alkylating agents, anthracyclines, antibiotics, antimitotic agents, procarbazine, hydroxyurea, asparaginase, corticosteroids, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

In certain embodiments, the methods of the present invention comprise administration of a third therapeutic agent selected from the group consisting of radiation, surgery, a cancer vaccine, a PD-L1 inhibitor (e.g., an anti-PD-L1 antibody), a LAG-3 inhibitor, a CTLA-4 inhibitor (e.g., ipilimumab), a TIM3 inhibitor, a BTLA inhibitor, a TIGIT inhibitor, a CD47 inhibitor, an antagonist of another T-cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGF.beta.) inhibitor, an epidermal growth factor receptor (EGFR) inhibitor (e.g., erlotinib, cetuximab), an agonist to a co-stimulatory receptor (e.g., an agonist to glucocorticoid-induced TNFR-related protein), an antibody to a tumor-specific antigen (e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9), a vaccine (e.g., *Bacillus* Calmette-Guerin, a cancer vaccine), an adjuvant to increase antigen presentation (e.g., granulocyte-macrophage colony-stimulating factor), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), radiotherapy, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), chimeric antigen receptor T cells (e.g., CD19-targeted T cells), an anti-inflammatory drug (e.g., corticosteroids, and non-steroidal anti-inflammatory drugs), and a dietary supplement such as anti-oxidants.

In certain embodiments, the methods of the invention comprise administering an anti-PD-1 antibody and an anti-MUC16/anti-CD3 bispecific antibody in combination with radiation therapy to generate long-term durable anti-tumor responses and/or enhance survival of patients with cancer.

In some embodiments, the methods of the invention comprise administering radiation therapy prior to, concomitantly or after administering an anti-PD-1 antibody and a bispecific anti-MUC16/anti-CD3 antibody to a cancer patient. For example, radiation therapy may be administered in one or more doses to tumor lesions after administration of one or more doses of the antibodies. In some embodiments, radiation therapy may be administered locally to a tumor lesion to enhance the local immunogenicity of a patient's tumor (adjuvinating radiation) and/or to kill tumor cells (ablative radiation) after systemic administration of an anti-PD-1 antibody and/or a bispecific anti-MUC16/anti-CD3 antibody. In certain embodiments, the antibodies may be administered in combination with radiation therapy and a chemotherapeutic agent (e.g., carboplatin and/or paclitaxel) or a VEGF antagonist (e.g., aflibercept).

Pharmaceutical Compositions and Administration

The present invention includes methods which comprise administering an anti-PD-1 antibody in combination with a bispecific anti-MUC16/anti-CD3 antibody to a subject wherein the antibodies are contained within separate or combined (single) pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: *Remington's Pharmaceutical Sciences*, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, *Medical Applications of Controlled Release*, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Administration Regimens

The present invention includes methods comprising administering to a subject an anti-PD-1 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the present invention includes methods comprising administering to a subject a bispecific anti-MUC16/anti-CD3 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the methods involve the administration of an anti-PD-1 antibody in combination with a bispecific anti-MUC16/anti-CD3 antibody at a dosing frequency of about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

According to certain embodiments of the present invention, multiple doses of an anti-PD-1 antibody in combination with a bispecific anti-MUC16/anti-CD3 antibody may be administered to a subject over a defined time course. The methods according to this aspect of the invention comprise sequentially administering to a subject one or more doses of an anti-PD-1 antibody in combination with one or more doses of a bispecific anti-MUC16/anti-CD3 antibody. As used herein, "sequentially administering" means that each dose of the antibody is administered to the subject at a different point in time, e.g., on different days separated by a predetermined interval (e.g., hours, days, weeks or months). The present invention includes methods which comprise sequentially administering to the patient a single initial dose of an anti-PD-1 antibody, followed by one or more secondary doses of the anti-PD-1 antibody, and optionally followed by one or more tertiary doses of the anti-PD-1 antibody. In certain embodiments, the methods further comprise sequentially administering to the patient a single initial dose of a bispecific anti-MUC16/anti-CD3 antibody, followed by one or more secondary doses of the bispecific antibody, and optionally followed by one or more tertiary doses of the bispecific antibody.

According to certain embodiments of the present invention, multiple doses of an anti-PD-1 antibody and a bispecific anti-MUC16/anti-CD3 antibody may be administered to a subject over a defined time course. The methods according to this aspect of the invention comprise sequentially administering to a subject multiple doses of an anti-PD-1 antibody and a bispecific anti-MUC16/anti-CD3 antibody. As used herein, "sequentially administering" means that each dose of the anti-PD-1 antibody in combination with the bispecific antibody is administered to the subject at a different point in time, e.g., on different days separated by a predetermined interval (e.g., hours, days, weeks or months).

The terms "initial dose," "secondary doses," and "tertiary doses," refer to the temporal sequence of administration. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antibody (anti-PD-1 antibody or bispecific antibody). In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an anti-PD-1 antibody may be administered to a patient with an ovarian cancer at a loading dose of about 1-3 mg/kg followed by one or more maintenance doses of about 0.1 to about 20 mg/kg of the patient's body weight.

In one exemplary embodiment of the present invention, each secondary and/or tertiary dose is administered 1/2 to 14 (e.g., 1/2, 1, 11/2, 2, 21/2, 3, 31/2, 4, 41/2, 5, 51/2, 6, 61/2, 7, 71/2, 8, 81/2, 9, 91/2, 10, 101/2, 11, 111/2, 12, 121/2, 13, 131/2, 14, 141/2, or more) weeks after the immediately preceding dose. The phrase "the immediately preceding dose," as used herein, means, in a sequence of multiple administrations, the dose of anti-PD-1 antibody (and/or bispecific anti-MUC16/anti-CD3 antibody) which is administered to a patient prior to the administration of the very next dose in the sequence with no intervening doses.

The methods according to this aspect of the invention may comprise administering to a patient any number of secondary and/or tertiary doses of an anti-PD-1 antibody (and/or bispecific anti-MUC16/anti-CD3 antibody). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, one or more doses of an anti-PD-1 antibody and/or a bispecific anti-MUC16/anti-CD3 antibody are administered at the beginning of a treatment regimen as "induction doses" on a more frequent basis (twice a week, once a week or once in 2 weeks) followed by subsequent doses ("consolidation doses" or "maintenance doses") that are administered on a less frequent basis (e.g., once in 4-12 weeks).

The present invention includes methods comprising sequential administration of an anti-PD-1 antibody in combination with a bispecific anti-MUC16/anti-CD3 antibody, to a patient to treat an ovarian cancer (e.g., serous cancer). In some embodiments, the present methods comprise administering one or more doses of an anti-PD-1 antibody followed by one or more doses of a bispecific anti-MUC16/anti-CD3 antibody. In certain embodiments, the present methods comprise administering a single dose of an anti-PD-1 antibody followed by one or more doses of a bispecific anti-MUC16/anti-CD3 antibody. In some embodiments, one or more doses of about 0.1 mg/kg to about 20 mg/kg of an anti-PD-1 antibody may be administered followed by one or more doses of about 0.1 mg/kg to about 20 mg/kg of the bispecific antibody to inhibit tumor growth and/or to prevent tumor recurrence in a subject with an ovarian cancer. In some embodiments, the anti-PD-1 antibody is administered at one or more doses followed by one or more doses of the bispecific antibody resulting in increased anti-tumor efficacy (e.g., greater inhibition of tumor growth, increased prevention of tumor recurrence as compared to an untreated subject or a subject administered with either antibody as monotherapy). Alternative embodiments of the invention pertain to concomitant administration of anti-PD-1 antibody and the bispecific antibody which is administered at a separate dosage at a similar or different frequency relative to the anti-PD-1 antibody. In some embodiments, the bispecific antibody is administered before, after or concurrently with the anti-PD-1 antibody. In certain embodiments, the bispecific antibody is administered as a single dosage formulation with the anti-PD-1 antibody.

Dosage

The amount of anti-PD-1 antibody and/or bispecific anti-MUC16/anti-CD3 antibody administered to a subject according to the methods of the present invention is, generally, a therapeutically effective amount. As used herein, the phrase "therapeutically effective amount" means an amount of antibody (anti-PD-1 antibody or bispecific anti-MUC16/anti-CD3 antibody) that results in one or more of: (a) a reduction in the severity or duration of a symptom of a cancer (e.g., ovarian cancer); (b) inhibition of tumor growth, or an increase in tumor necrosis, tumor shrinkage and/or tumor disappearance; (c) delay in tumor growth and development; (d) inhibit or retard or stop tumor metastasis; (e) prevention of recurrence of tumor growth; (f) increase in survival of a subject with cancer (e.g., ovarian cancer); and/or (g) a reduction in the use or need for conventional anti-cancer therapy (e.g., reduced or eliminated use of chemotherapeutic or cytotoxic agents) as compared to an untreated subject or a subject administered with either antibody as monotherapy.

In the case of an anti-PD-1 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PD-1 antibody. In certain embodiments, 250 mg of an anti-PD-1 antibody is administered.

In the case of a bispecific anti-MUC16/anti-CD3 antibody, a therapeutically effective amount can be from about 10 micrograms (mcg) to about 8000 mcg, e.g., about 10 mcg, about 20 mcg, about 50 mcg, about 70 mcg, about 100 mcg, about 120 mcg, about 150 mcg, about 200 mcg, about 250 mcg, about 300 mcg, about 350 mcg, about 400 mcg, about 450 mcg, about 500 mcg, about 550 mcg, about 600 mcg, about 700 mcg, about 800 mcg, about 900 mcg, about 1000 mcg, about 1050 mcg, about 1100 mcg, about 1500 mcg, about 1700 mcg, about 2000 mcg, about 2050 mcg, about 2100 mcg, about 2200 mcg, about 2500 mcg, about 2700 mcg, about 2800 mcg, about 2900 mcg, about 3000 mcg, about 4000 mcg, about 5000 mcg, about 6000 mcg, about 7000 mcg, or about 8000 mcg of the bispecific anti-MUC16/anti-CD3 antibody.

The amount of either anti-PD-1 antibody or bispecific anti-MUC16/anti-CD3 antibody contained within the individual doses may be expressed in terms of milligrams of antibody per kilogram of subject body weight (i.e., mg/kg). In certain embodiments, either anti-PD-1 antibody or bispecific anti-MUC16/anti-CD3 antibody used in the methods of the present invention may be administered to a subject at a dose of about 0.0001 to about 100 mg/kg of subject body weight. For example, anti-PD-1 antibody may be administered at dose of about 0.1 mg/kg to about 20 mg/kg of a patient's body weight. The bispecific anti-MUC16/anti-CD3 antibody may be administered at a dose of about 0.1 mg/kg to about 20 mg/kg of a patient's body weight.

A summary of the sequences and the corresponding SEQ ID NOs referenced herein is shown in Table 1, below.

TABLE 1

Summary of Sequences

| SEQ ID NO: | Description |
|---|---|
| 1 | Anti-MUC16 Heavy Chain Variable Region |
| 2 | Anti-MUC16 and Anti-CD3 Light Chain Variable Region |
| 3 | Anti-CD3-G Heavy Chain Variable Region |
| 4 | Anti-CD3-G5 Heavy Chain Variable Region |
| 5 | Anti-CD3-G9 Heavy Chain Variable Region |
| 6 | Anti-CD3-G10 Heavy Chain Variable Region |
| 7 | Anti-CD3-G20 Heavy Chain Variable Region |
| 8 | Anti-MUC16 HCDR1 |
| 9 | Anti-MUC16 HCDR2 |
| 10 | Anti-MUC16 HCDR3 |
| 11 | Anti-MUC16 and Anti-CD3 LCDR1 |
| 12 | Anti-MUC16 and Anti-CD3 LCDR2 |
| 13 | Anti-MUC16 and Anti-CD3 LCDR3 |
| 14 | Anti-CD3-G HCDR1 |
| 15 | Anti-CD3-G HCDR2 |
| 16 | Anti-CD3-G HCDR3 |
| 17 | Anti-CD3-G5 HCDR1 |
| 18 | Anti-CD3-G5 HCDR2 |
| 19 | Anti-CD3-G5 HCDR3 |
| 20 | Anti-CD3-G9 HCDR1 |
| 21 | Anti-CD3-G9 HCDR2 |
| 22 | Anti-CD3-G9 HCDR3 |
| 23 | Anti-CD3-G10 HCDR1 |
| 24 | Anti-CD3-G10 HCDR2 |
| 25 | Anti-CD3-G10 HCDR3 |
| 26 | Anti-CD3-G20 HCDR1 |
| 27 | Anti-CD3-G20 HCDR2 |
| 28 | Anti-CD3-G20 HCDR3 |
| 29 | Anti-MUC16 Heavy Chain |
| 30 | Anti-MUC16 and Anti-CD3 Light Chain |
| 31 | Anti-CD3-G Heavy Chain |
| 32 | Anti-CD3-G20 Heavy Chain |
| 33 | Anti-PD-1 Heavy Chain Variable Region |

TABLE 1-continued

Summary of Sequences

| SEQ ID NO: | Description |
|---|---|
| 34 | Anti-PD-1 Light Chain Variable Region |
| 35 | Anti-PD-1 HCDR1 |
| 36 | Anti-PD-1 HCDR2 |
| 37 | Anti-PD-1 HCDR3 |
| 38 | Anti-PD-1 LCDR1 |
| 39 | Anti-PD-1 LCDR2 |
| 40 | Anti-PD-1 LCDR3 |
| 41 | Anti-PD-1 Heavy Chain |
| 42 | Anti-PD-1 Light Chain |

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Bispecific Antibodies that Bind Ovarian Cell-Specific (MUC16) and CD3

The present invention provides bispecific antigen-binding molecules that bind CD3 and MUC16; such bispecific antigen-binding molecules are also referred to herein as "anti-MUC16/anti-CD3 or anti-MUC16×CD3 bispecific molecules." The anti-MUC16 portion of the anti-MUC16/anti-CD3 bispecific molecule is useful for targeting tumor cells that express MUC16 (also known as CA-125), and the anti-CD3 portion of the bispecific molecule is useful for activating T-cells. The simultaneous binding of MUC16 on a tumor cell and CD3 on a T-cell facilitates directed killing (cell lysis) of the targeted tumor cell by the activated T-cell.

Bispecific antibodies comprising an anti-MUC16-specific binding domain and an anti-CD3-specific binding domain were constructed using standard methodologies, wherein the anti-MUC16 antigen binding domain and the anti-CD3 antigen binding domain each comprise different, distinct HCVRs paired with a common LCVR. In exemplified bispecific antibodies, the molecules were constructed utilizing a heavy chain from an anti-CD3 antibody, a heavy chain from an anti-MUC16 antibody and a common light chain from the anti-MUC16 antibody. In other instances, the bispecific antibodies may be constructed utilizing a heavy chain from an anti-CD3 antibody, a heavy chain from an anti-MUC16 antibody and a light chain from an anti-CD3 antibody or an antibody light chain known to be promiscuous or pair effectively with a variety of heavy chain arms.

Exemplified bispecific antibodies were manufactured having an IgG1 Fc domain (BSMUC16/CD3-001, -002, -003, and -004) or a modified (chimeric) IgG4 Fc domain (BSMUC16/CD3-005) as set forth in US Patent Application Publication No. US20140243504A1, published on Aug. 28, 2014.

A summary of the component parts of the antigen-binding domains of the various anti-MUC16×CD3 bispecific antibodies constructed is set forth in Table 2.

TABLE 2

Summary of Component Parts of Anti-MUC16×CD3 Bispecific Antibodies

| Bispecific Antibody Identifier | Anti-MUC16 Antigen-Binding Domain Heavy Chain Variable Region | Anti-CD3 Antigen-Binding Domain Heavy Chain Variable Region | Common Light Chain Variable Region |
|---|---|---|---|
| BSMUC16/CD3-001 | (SEQ ID NO: 1) | CD3-VH-G (SEQ ID NO: 3) | (SEQ ID NO: 2) |
| BSMUC16/CD3-002 | (SEQ ID NO: 1) | CD3-VH-G5 (SEQ ID NO: 4) | (SEQ ID NO: 2) |
| BSMUC16/CD3-003 | (SEQ ID NO: 1) | CD3-VH-G9 (SEQ ID NO: 5) | (SEQ ID NO: 2) |
| BSMUC16/CD3-004 | (SEQ ID NO: 1) | CD3-VH-G10 (SEQ ID NO: 6) | (SEQ ID NO: 2) |
| BSMUC16/CD3-005 | (SEQ ID NO: 1) | CD3-VH-G20 (SEQ ID NO: 7) | (SEQ ID NO: 2) |

Example 2: CA-125 does not Interfere with Anti-MUC16×CD3 Antibody Activity In Vitro The impact of soluble CA-125 (the shed form of MUC16) on the activity of BSMUC16/CD3-001 was Assessed Using FACS Binding and Cytotoxicity Assays in the Presence of High Levels of CA-125 purified from ascites of ovarian cancer patients. CA-125 levels are increased in the serum of the majority of ovarian cancer patients and circulating levels could impact any MUC16-targeted therapy by acting as an antigen sink. The levels of CA-125 used in the assay (10,000 U/ml) greatly exceed the median published levels of 656.6 U/mL in ovarian cancer patients. The ability of BSMUC16/CD3-001 to kill MUC16-expressing OVCAR-3 cells in the presence of soluble CA-125 enriched from human ascites (creative Biomart, N.Y., USA) or a membrane proximal construct expressing the five carboxy-terminal SEA domains and the juxtamembrane region of MUC16 (MUC16Δ) was carried out at an Effector/Target ratio of 4:1 with a fixed concentration of BSMUC16/CD3-001 or CD3-binding control antibody (100 pM), and a serial dilution of either MUC16-1H or MUC16Δ for 72 hours at 37° C. In order to monitor the specific killing of MUC16-bearing target cells, OVCAR-3 cells were labeled with 1 uM of Violet Cell Tracker. After labeling, cells were plated overnight at 37° C. Separately, human PBMCs were plated in supplemented RPMI media at 1×10$^6$ cells/mL and incubated overnight at 37° C. in order to enrich for lymphocytes by depleting adherent cells. The next day, target cells were co-incubated with adherent cell-depleted naïve PBMC (Effector/Target cell ratio 4:1) and a serial dilution of either BSMUC16/CD3-001 or the CD3-binding control for 72 hours at 37° C. Cells were removed from cell culture plates using trypsin, and analyzed by FACS. For FACS analysis, cells were stained with a dead/live far red cell tracker (Invitrogen). For the assessment of specificity of killing, cells were gated on Violet cell tracker labeled populations. Percent of live target cells was reported for the calculation of adjusted survival as follows: Adjusted survival=(R1/R2)*100, where R1=% live target cells in the presence of antibody, and R2=% live target cells in the absence of test antibody. T cell activation was assessed by incubating cells with directly conjugated antibodies to CD2, CD69, and CD25, and by reporting the percent of activated (CD69+) T cells or (CD25+) T cells out of total T cells (CD2+).

The binding of BSMUC16/CD3-001 and an antibody known to bind CA-125 (clone 3A5) to CA125 obtained from human ascites fluid was measured by enzyme-linked immunosorbent assay (ELISA). Briefly, soluble CA-125 (creative Biomart, N.Y., USA) at a concentration of 4000 units/mL in PBS was passively adsorbed to a 96-well microtiter plates overnight at 4° C. The plates were then washed with PBST and blocked with 0.5% BSA in PBS for 1 hour. Biotinylated BSMUC16/CD3-001, the MUC16 parental antibody, a-MUC16 3A5 and non-binding controls (BSMUC16/CD3-001 isotype control and a-MUC16 3A5 isotype control), were added to plate at concentrations of 10, 1, 0.3, or 0.1 nM in 0.5% BSA in PBS for 1 hour, followed by a wash with PBST. Streptavidin conjugated with horseradish peroxidase (SA-HRP) (ThermoFisher Scientific, Waltham, Mass., USA) at 1:10000 dilution of 1.0 mg/mL stock solution was added to the wells and incubated for 1 hour to detect plate-bound biotinylated antibodies. The plate was washed and developed with 3-3', 5-5'-tetramethylbenzidine (BD Biosciences, Franklin Lakes, N.J., USA) substrate according the manufacturer's instructions. Absorbance at 450 nm was recorded for each well on a Victor Multilabel Plate Reader (Perkin Elmer; Melville, N.Y.). Data were analyzed with GraphPad Prism software.

Excess CA-125 had minimal impact on BSMUC16/CD3-0001 binding to OVCAR-3 cells suggesting minimal binding to CA-125 (FIG. 1). In contrast, CA-125 greatly inhibited the ability of a comparator antibody that likely binds to the repeat region of MUC16 (in-house version of antibody clone 3A) (FIG. 1). Further, a soluble MUC16 construct containing the membrane-proximal region up to the 5th SEA domain of MUC16 (MUC16Δ) dramatically inhibited binding of BSMUC16/CD3-001, showing that BSMUC16/CD3-001 binds a membrane proximal region, as discussed in greater detail in WO 2018/067331, which is herein incorporated by reference. In alignment with the binding studies, BSMUC16/CD3-001 could also induce T cell-mediated killing in the presence of CA-125, but not in the presence of a high concentration of MUC16Δ (data not shown). Thus, BSMUC16/CD3-001 can bind to MUC16 and induce T cell redirected killing even in the presence of high concentrations of CA-125.

Example 3: PD-1 Blockade Enhances Anti-Tumor Activity of Anti-MUC16×CD3 Bispecific Antibodies in Xenogenic and Syngeneic Tumor Models The in vivo efficacy of an anti-MUC16/anti-CD3 bispecific antibody in combination with PD-1 blockade was evaluated in xenogenic and syngeneic tumor models.

A. Xenogenic Model—OVCAR-3/Luc

For the xenogenic model, immunodeficient NSG mice were injected intraperitoneally (IP) with OVCAR-3/Luc cells previously passaged in vivo (Day 0) thirteen days after engraftment with human PBMCs. Mice were treated IP with 12.5 ug/mouse BSMUC16/CD3-001, or administered 12.5 ug CD3-binding control alone or in combination with 100 ug REGN2810 on Days 5 and 8. Tumor burden was assessed by BLI on Days 4, 8, 12, 15, 20 and 25 post tumor implantation. As determined by BLI measurements on Day 25, treatment with 12.5 ug of BSMUC16/CD3-001 resulted in significant anti-tumor efficacy as determined by BLI measurements and combination with REGN2810 (anti-PD-1) further enhanced the anti-tumor efficacy. All groups had similar tumor burden as assessed by BLI before dosing started. There was no significant difference in tumor burden between groups.

BSMUC16/CD3-001 significantly reduces tumor burden at 12.5 ug and addition of anti-PD-1 enhances the anti-tumor efficacy over that of BSMUC16/CD3-001 alone. NSG mice engrafted with human T cells were implanted with human OVCAR-3/Luc cells. Mice were treated on Days 5 and 8 with 12.5 ug BSMUC16/CD3-001 administered IV or treated with a CD3-binding control or non-binding control (12.5 ug IV). Data shown in Table 3, below, is tumor burden as assessed by BLI on Day 25 post tumor implantation. Statistical significance was determined using unpaired non-parametric Mann-Whitney t-tests. Treatment with BSMUC16/CD3-001+/−REGN2810 was compared to the CD3-binding control (* p<0.05 for BSMUC16/CD3-001, ** p<0.01 for BSMUC16/CD3-001 and REGN2810) and treatment with BSMUC16/CD3-001 alone was compared to combination with REGN2810 (#p<0.05).

TABLE 3

| Bioluminescence on Day 25 post tumor implantation | |
|---|---|
| Antibody (ug) | Avg Radiance [p/s/cm$^2$/sr] 25 days post-implantation (median ± SEM) |
| hIgG4P-PVA CD3-binding Control (12) | 7.71e+06 ± 1.07e+06 |
| BSMUC16/CD3-001 (12) | 7.44e+03 ± 3.11e+03 |
| hIgG4P-PVA CD3-binding Control (12) + REGN2810 (100) | 9.29e+06 ± 1.82e+06 |
| BSMUC16/CD3-001 (12) + REGN2810 (100) | 1.76e+03 ± 9.38e+01 |

B. Syngeneic Model—ID8-VEGF/huMUC16

To examine efficacy in an immune-competent model, the murine CD3 gene was replaced with human CD3 and a portion of the mouse MUC16 gene was replaced with the human sequence. The replacements resulted in a mouse whose T cells express human CD3 and that expresses a chimeric MUC16 molecule containing a portion of human MUC16 where the BSMUC16/CD3-001 and BSMUC16/CD3-005 bispecific antibodies bind.

For this first syngeneic tumor model, the ID8-VEGF cell line engineered to express the portion of human MUC16 was used. Mice were implanted with the ID8-VEGF/huMUC16 cells IP and treated with 5 mg/kg of BSMUC16/CD3-001 or CD3-binding control with isotype control or in combination with anti-PD-1 (5 mg/kg IV) three days after implantation. Treatment with BSMUC16/CD3-001 extended the median survival compared to the group that received the CD3-binding control but the addition of anti-PD-1 blockade also resulted in survival of 50% of the mice. BSMUC16/CD3-001 significantly increases median survival time in an ID8-VEGF ascites model and addition of PD-1 (REGN2810) blockade allows survival of several mice. Mice expressing human CD3 in place of mouse CD3 and a chimeric MUC16 molecule were implanted with the murine ovarian tumor line expressing a portion of human MUC16. Mice were administered BSMUC16/CD3-001 (5 mg/kg IV) or administered CD3-binding control (5 mg/kg IV) with isotype control or with anti-PD-1 on day 3 post implantation. Mice were treated on Days 3, 7, 10, 14, 17 post tumor implantation. Data shown is median survival. Mice were sacrificed when they had a with weight-gain of more than 20% due to ascites-induced abdominal distension. Statistical significance was determined using the Mantel-Cox method. Both BSMUC16/CD3-001 and BSMUC16/CD3-001+anti-PD-1 treatment resulted in an increase in median survival time and the combination of BSMUC16/CD3-001+anti-PD-1 resulted in 50% survival, demonstrating a synergistic effect between the MUC16×CD3 bispecific antibody and the anti-PD-1 antibody. Results are shown in Table 4, below.

TABLE 4

Median Survival in the ID8-VEGF/huMUC16 model

| Antibody (mg/kg) | Median Survival (Days) |
|---|---|
| CD3-binding control (5) + isotype control (5) | 36 |
| BSMUC16/CD3-001 (5) + isotype control (5) | 46 |
| CD3-binding control (5) + PD-1 (5) | 32 |
| BSMUC16/CD3-001 (5) + PD-1 (5) | 69.5 |

Similar results were observed when BSMUC16/CD3-001 was administered at 1 mg/kg in combination with the anti-PD-1 antibody.

C. Syngeneic Model—MC38/huMUC16

As discussed above, the mice used in this experiment were engineered so that the murine CD3 gene was replaced with human CD3 and a portion of the mouse MUC16 gene was replaced with the human sequence. The replacements resulted in a mouse whose T cells express human CD3 and that expresses a chimeric MUC16 molecule containing a portion of human MUC16 where the BSMUC16/CD3-001 and BSMUC16/CD3-005 bispecific antibody binds.

For this second syngeneic tumor model, the MC38 line engineered to express the portion of human MUC16 was used. Mice were implanted with MC38/huMUC16 cells SC and treated with BSMUC16/CD3-005 or CD3-binding control with isotype control (1 mg/kg IV) or in combination with anti-PD-1 (5 mg/kg IV) on Day 7 post tumor implantation. The anti-PD-1 antibody used in this experiment was a commercially available murine antibody (clone RMP1-14, BioXCell). The combination of BSMUC16/CD3-005 and anti-PD-1 showed a synergistic anti-tumor effect.

Figure 2:
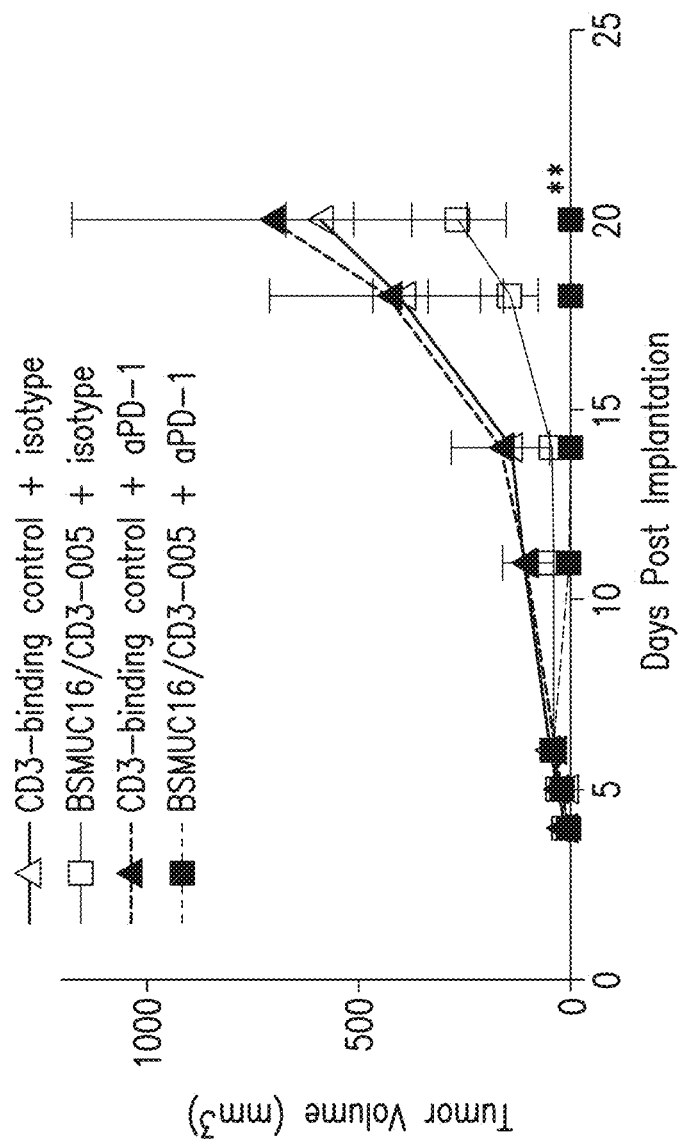
FIG. 2 illustrates the mean tumor growth curves for groups of mice (5 per group) treated with CD3-binding control+isotype control (Δ), BSMUC16/CD3-005+isotype control (□), CD3-binding control+anti-PD-1 (▲), and BSMUC16/CD3-005+anti-PD-1 (■) (as described in Example 3 herein). The combination of an anti-PD-1 antibody and an anti-CD3×MUC16 bispecific antibody synergistically inhibited tumor growth.

The combination of BSMUC16/CD3-005 and anti-PD-1 blockade resulted in better anti-tumor efficacy than BSMUC16/CD3-005 alone in a MC38 SC model. Mice expressing human CD3 in place of mouse CD3 and a chimeric MUC16 molecule were implanted with the murine tumor line MC38 expressing a portion of human MUC16. Mice were administered BSMUC16/CD3-005 or administered CD3-binding control (1 mg/kg IV) with isotype control or with anti-PD-1 antibody (5 mg/kg IV) on day 7 post implantation. Mice were treated on Days 7, 11 and 14 post tumor implantation. The results are illustrated in FIG. 2. Statistical significance was determined using two-way ANOVA with Tukey's multiple comparison test. BSMUC16/CD3-005 plus anti-PD-1 significantly, and synergistically, inhibited tumor growth over the CD3-binding control.

Example 4: Immuno-PET Imaging in Engineered Mice Showed Localization of the Anti-MUC16×CD3 Bispecific Antibody to T Cell-Rich Organs The in vivo localization of BSMUC16/CD3-001 and BSMUC16/CD3-005 and the expression of MUC16 protein were assessed in wild type and genetically humanized mice using PET imaging. The biodistribution of the $^{89}$Zr-labelled anti-MUC16 antibody (bivalent anti-MUC16 antibody generated using the same anti-MUC16 heavy and light chain as the bispecifics, herein referred to as "parental") was similar in both wild type and humanized mice, suggesting low expression/availability of the humanized MUC16 protein to the antibody. In contrast, when mice were administered therapeutically relevant doses of a $^{89}$Zr-labelled BSMUC16/CD3-001 bispecific antibody, distribution to the spleen and lymph nodes was evident due to recognition of CD3 positive T cells in these lymphoid organs (data not shown). Ex vivo biodistribution analyses in individual tissues confirmed localization to lymph nodes and spleen (data not shown). Uptake of $^{89}$Zr-labelled BSMUC16/CD3-005 bispecific antibody in lymphoid tissues was greatly reduced relative to BSMUC16/CD3-001 due to its lower affinity for CD3. To assess whether BSMUC16/CD3-001 and BSMUC16/CD3-005 can accumulate in MUC16-expressing tumors, $^{89}$Zr-labelled BSMUC16/CD3-001 and $^{89}$Zr-labelled BSMUC16/CD3-005 were administered to mice bearing ID8-VEGF-huMUC16Δ tumors. Tumor uptake between the bispecific antibodies was not significantly different despite the higher lymphoid uptake of BSMUC16/CD3-001 (data not shown).

Preparation of Immunoconjugate and Small Animal PET:

BSMUC16/CD3-001 and control antibody were conjugated with DFO to glutamine residues at position 295 via transamidation by microbial transglutaminase following deglycosylation of the antibodies with PNGase F. DFO conjugated antibodies were then chelated with Zirconium-89 ($^{89}$Zr). Mice received antibody at a final dose of 0.5 mg/kg via tail vein injection. PET imaging was then performed to assess in vivo localization of the radioimmunoconjugate at day 6 post dosing, prior to ex vivo biodistribution studies. For experiments in tumor-bearing mice, mice were implanted subcutaneously with 10×10$^6$ ID8-VEGF-huMUC16Δ tumor cells. Tumor bearing mice were dosed with $^{89}$Zr radiolabeled antibodies 20 day post implantation when tumors averaged 150 mm$^3$.

A pre-calibrated Sofie Biosciences G8 PET/CT instrument (Sofie Biosciences (Culver city, CA) and Perkin Elmer) was used to acquire PET and CT images. The energy window ranged from 150 to 650 keV with a reconstructed resolution of 1.4 mm at the center of the field of view. On day 6 post dosing, mice underwent induction anesthesia using isoflurane and were kept under continuous flow of isoflurane during a 10-minute static PET acquisition. CT images were acquired following PET acquisition. The PET image was subsequently reconstructed using pre-configured settings. Decay-corrected PET data and CT data were processed using VivoQuant software (inviCRO Imaging Services) into false-colored co-registered PET-CT maximum intensity projections on a color scale calibrated to indicate a signal range of 0 to 30% of injected dose per volume, expressed as % ID/g. For ex vivo biodistribution analysis, mice were euthanized following imaging on day 6 post dosing. Blood was collected via cardiac puncture into counting tubes. Normal tissues (inguinal and axillary lymph nodes, thymus, spleen, heart, lungs, stomach, small intestine, liver, kidneys, bone and ovary) were then excised and placed into counting tubes. Tumors were similarly collected into counting tubes. All tubes had been pre-weighed and were subsequently re-weighed to determine the weight of the blood and tissues. The γ-emission radioactivity for all samples were then counted on an automatic gamma counter (Wizard 2470, Perkin Elmer) and results reported in in counts per minute (cpm). The % ID for each sample was the determined using samples counts relative to dose-standards counts prepared from the original injected material. Subsequently, the individual % ID/g values were derived by dividing the % ID value by the respective weight of the appropriate blood, tissues or tumor sample.

$^{89}$Zr-labeled BSMUC16/CD3-001 and $^{89}$Zr-labeled BSMUC16/CD3-005 demonstrated specific localization to MUC16+ tumors and CD3+ lymphoid tissues, with lymphoid distribution correlating to relative CD3 affinity. Both MUC16×CD3 bispecifics demonstrated equivalent tumor localization in the presence of CD3+ tissues.

Example 5: Toxicology Studies in Cynomolgus Monkeys Showed No Overt Toxicity for the Anti-MUC16×CD3 Bispecific Antibody BSMUC16/CD3-001 cross-reacts with monkey MUC16 and CD3. To determine the safety and tolerability, and characterize the pharmacokinetics of the bispecific antibody, a multidose toxicity study was conducted in cynomolgus monkeys. Six monkeys/sex/group received weekly administration of BSMUC16/CD3-001 for a total of five doses at 0.01, 0.1 or 1 mg/kg. At the completion of the dosing period, 3 animals/sex/group were euthanized and tissues examined for microscopic finding, while the remaining three animals/sex/group underwent 12 weeks of treatment-free recovery to assess the reversibility or persistence of any BSMUC16/CD3-001-related effects. BSMUC16/CD3-001 was well tolerated, and all animals survived to the time of scheduled necropsy. Toxicokinetic analysis demonstrated dose-proportional exposures and linear kinetics across the dose groups, with no gender differences observed (data not shown). Continuous exposure to BSMUC16/CD3-001 was observed throughout the dosing phase, and BSMUC16/CD3-001 exposure was maintained until the end of the recovery phase in all (n=6) and 50% of animals in the 0.1 and 1.0 mg/kg groups, respectively. BSMUC16/CD3-001 was not detected in the serum in any animal in the 0.01 mg/kg group after recovery week 8. The elimination half-life of BSMUC16/CD3-001 was approximately 10 days.

There were no BSMUC16/CD3-001-related clinical observations, nor any changes in urinalysis parameters, peripheral blood immunophenotyping, food consumption, or body weight during the dosing or recovery periods. Importantly, BSMUC16/CD3-001 administration did not result in any changes in respiratory, neurologic, or cardiovascular safety pharmacology evaluations, including no changes in ECG parameters. No BSMUC16/CD3-001-related changes in organ weight were found, nor were any macroscopic changes noted at either terminal or recovery necropsy. Dose-related, reversible elevations of circulating inflammatory markers (C-reactive protein (CRP) and IL-6) were observed within 1 day after the initial dose of either 1.0 or 0.1 mg/kg, but these elevations were not apparent after subsequent doses (data not shown). In accordance with the minimal increase of serum cytokines, T cell redistribution was not detected after BSMUC16/CD3-001 administration (data not shown), in contrast to what has been described for several CD3 bispecific molecules against hematological tumors.

The cynomolgus monkey study was conducted in accordance to guidelines of the IACUC. Cynomolgus monkeys (6 animals/sex/group) were administered control article (diluted placebo) or BSMUC16/CD3-001 (0.01, 0.1, or 1 mg/kg) once weekly via a 30-minute IV infusion. The control article was 10 mM histidine with 10% sucrose and 0.05% polysorbate 20, pH 6, diluted with 0.9% sodium chloride for injection, USP (sterile saline). Blood samples or tissues were collected at various time points for clinical pathology and histopathology. BSMUC16/CD3-001 concentration was determined by ELISA and toxicokinetic analysis was performed using WinNonLin software. CRP was analyzed on a Roche Modular P 800 system. Cytokines were measured by MSD (Meso Scale Diagnostics, Rockville, Md.). T cells were quantitated using flow cytometry. Briefly, blood was collected in potassium EDTA tubes, lysed, stained for CD3, CD4 and CD8 (BD Biosciences) and relative values for each phenotype are determined using a FACS Canto II. These values are then multiplied by the absolute lymphocyte values (via hematology analysis) to enumerate absolute cell counts for each phenotype.

Immunohistochemical staining for MUC16 was present in expected tissues: pancreas (mesothelium, ductal epithelium), heart and ovary (data not shown) as well as salivary gland (goblet cells), liver (mesothelium, bile duct), lung (mesothelium, bronchiolar/bronchial epithelium), small intestine (mesothelium), testis (mesothelium, rete testis/efferent duct) and tonsil (epithelium, mucous glands) (not shown). BSMUC16/CD3-001-related microscopic changes, evaluated by hematoxylin and eosin (H&E) histologic staining, included inflammation (infiltration of white blood cells) and increased mesothelial cell size and cellularity leading to non-adverse thickening of the serosal lining and/or submesothelial connective tissue of multiple thoracic and peritoneal organs. These changes were generally focal or multifocal in nature and were minimal to slight in severity and were considered to be on-target for BSMUC16/CD3-001, resulting from engagement of MUC16 expressed on serosal epithelial (mesothelial) cells and activation of T cells. Importantly, the serosal changes were reversed or trended towards reversal at the end of the recovery period (data not shown).

Toxicology studies in cynomolgus monkeys showed minimal and transient increases in serum cytokines and C-reactive protein following BSMUC16/CD3-001 administration, with no overt toxicity.

Example 6: Assessment of Serum Cytokine Induction in Tumor-Bearing Mice

Because cytokine release syndrome (CRS) is a frequent serious side effect of CD3 bispecific and CAR T cell therapies, a study to monitor serum cytokines in relevant models following treatment with BSMUC16/CD3-001 was conducted. In genetically humanized MUC16/CD3 mice without tumors, no serum cytokine response was evident upon BSMUC16/CD3-001 administration.

To assess in vivo T cell activation by BSMUC16/CD3-001, serum cytokine levels from tumor-bearing mice were measured. Serum samples were collected 4 hours after the first antibody dose in the 0.5 mg/kg BSMUC16/CD3-001, CD3-binding control, and non-binding control groups. Treatment with BSMUC16/CD3-001 activated T cells as determined by induction of IFNγ, TNFα, IL-2, IL-6, IL-8, and IL-10, compared to the non-binding control and the CD3-binding control (data not shown). BSMUC16/CD3-001-induced cytokine response required the presence of both T cells as well as OVCAR-3/Luc cells, as mice bearing only OVCAR3/Luc cells did not have detectable human IFNγ in the serum, and mice without tumor cells to provide MUC16 for cross-linking did not show an increase in serum IFNγ in response to BSMUC16/CD3-001 (data not shown).

Measurement of serum cytokine levels: T cell activation in response to treatment with BSMUC16/CD3-001 was assessed by measuring the serum concentrations of interferon γ (IFNγ), tumor necrosis factor α (TNFα), interleukin-2 (IL-2), IL-4, IL-6, IL-8, IL-10, IL-12p70, IL-13, and IL-1B four hours after the first 0.5 mg/kg dose. Cytokine levels were analyzed using V-plex Human ProInflammatory-10 Plex kit following the manufacturer's instructions (Meso Scale Diagnostics, Rockville, Mass.). Cytokines were measured in two separate studies with 4-6 mice per group.

Example 7: MUC16 Expression in Humanized Mice and Effect of Anti-MUC16×CD3 Bispecific Antibodies on MUC16-Positive Tissues To investigate the antitumor efficacy of BSMUC16/CD3-001 in a mouse with a fully intact immune system, mice were genetically engineered to express human CD3 on T cells and a region of MUC16 covering the antibody binding region, both in the endogenous murine loci (knock-in mice). To validate these mice, MUC16 expression was examined by both RT-PCR and IHC. RNA expression was detected in the trachea as well as low levels in the lung, heart, ovary, pancreas and bladder (data not shown), similar to published data on murine MUC16 expression. To assess MUC16 protein expression, IHC was performed on selected tissues using an anti-human MUC16 antibody that recognizes a membrane-proximal region of MUC16. MUC16 protein expression was confirmed in the surface epithelium of the ovary and stomach in these mice. MUC16 was also observed in the tracheal lining/epithelium as well as the submucosal glands, as has been described in humans (data not shown).

Histology on Mouse Tissues:

Tissues from humanized or WT mice were harvested and stained with an anti-MUC16 antibody binding the membrane proximal domain of MUC16 by IHC using the Ventana Discovery XT (Ventana; Tucson, Ariz.). 5 µm Paraffin sections were cut onto Superfrost PLUS slides and baked for an hour at 60° C. The immunohistochemical staining was performed on the Discovery XT Automated IHC staining system using the Ventana DAB Map detection kit. Deparaffinization was performed using EZ Prep solution at 75° C. for 8 minutes. Mild antigen retrieval was performed (95° C., 8 minutes followed by 100° C., 24 minutes) using Tris-EDTA buffer pH 9 (CC1) from Ventana. This was followed by multiple blocking steps. Tissue sections were incubated with the anti-MUC16 antibody (2 µg/ml) for 8 hours at RT. An isotype control antibody recognizing an irrelevant non-binding antibody was used as the negative control. Primary antibody and negative control were applied manually. Biotinylated Goat Anti-Human IgG (Jackson ImmunoResearch) was used as the secondary antibody (1 µg/ml) and samples were incubated for an hour at RT. The chromogenic signal was developed using the Ventana DAB MAP Kit. Slides were manually counterstained with Hematoxylin (2 minutes), dehydrated and coverslipped. Images were acquired on the Aperio AT 2 slide scanner (Leica Biosystems; Buffalo Grove, Ill.) and analyzed using Indica HALO software (Indica Labs; Corrales, N. Mex.). H&E staining were performed by Histoserv, Inc (Germantown, Md., USA).

The T cells in these mice are polyclonal, as assessed by T cell receptor (TCR) Vβ usage, express human CD3, and are present in similar numbers to wildtype mice (data not shown). To determine whether BSMUC16/CD3-001 induced any T cell activation or effects on normal tissues in these animals, non-tumor-bearing mice were injected with a high dose of BSMUC16/CD3-001 (10 mg/kg) and T cell numbers in blood, serum cytokines, and histopathology were then examined. Although T cells can be activated by an anti-human CD3 antibody (OKT3) as measured by T cell margination from the blood and increased levels of serum cytokines (data not shown), BSMUC16/CD3-001 did not induce any such effects, suggesting limited accessibility of the MUC16 target (data not shown). To determine whether BSMUC16/CD3-001 induced any microscopic changes in MUC16-expressing tissues, MUC16 and CD3 humanized mice received two doses of BSMUC16/CD3-001 at 10 mg/kg on Day 0 and Day 3. On day 5, several MUC16-expressing tissues (trachea, stomach and ovary) were examined, and no cellular infiltration or necrosis was seen in these tissues following BSMUC16/CD3-001 administration (data not shown). Histopathology examination revealed no inflammation or infiltration into MUC16-expressing tissues in mice after BSMUC16/CD3-001 administration at the time examined.

The results of this study, as well as the cynomolgus monkey study discussed in Example 5, demonstrate the safety profile of BSMUC16/CD3-001. BSMUC16/CD3-001 induced only minimal serum cytokines and, while there was focal induction of inflammation and thickening of the serosal lining in MUC16-expressing suggesting on-target activity, these effects were resolving by the end of the recovery period and consistent with inflammation and increased cellularity indicative of repair. The observed serosal changes were not correlated with any clinical observations, clinical pathology (except inflammatory response), or microscopic changes to the underlying parenchyma. Thus, studies in both genetically humanized mice and cynomolgus monkey show BSMUC16/CD3-001 was well-tolerated.

Example 8: Monitoring PD-1 Expression in a FACS-Based Cytotoxicity Assay Using Naïve Human Effector Cells In order to monitor the specific killing of Muc16-bearing target cells by flow cytometry, the ovarian cell line OVCAR-3 was labeled with 1 uM of Violet Cell Tracker. After labeling, cells were plated overnight at 37° C. Separately, human PBMCs were plated in supplemented RPMI media at $1 \times 10^6$ cells/mL and incubated overnight at 37° C. in order to enrich for lymphocytes by depleting adherent macrophages, dendritic cells, and some monocytes. The next day, target cells were co-incubated with adherent cell-depleted naïve PBMC (Effector/Target cell 4:1) and a serial dilution of either BSMUC16/CD3-001 or the CD3-binding control for 72 hours at 37° C. Cells were removed from cell culture plates using trypsin, and analyzed by FACS. For FACS analysis, cells were stained with a dead/live far red cell tracker (Invitrogen). For the assessment of specificity of killing, cells were gated on Violet cell tracker labeled populations.

Figure 3:
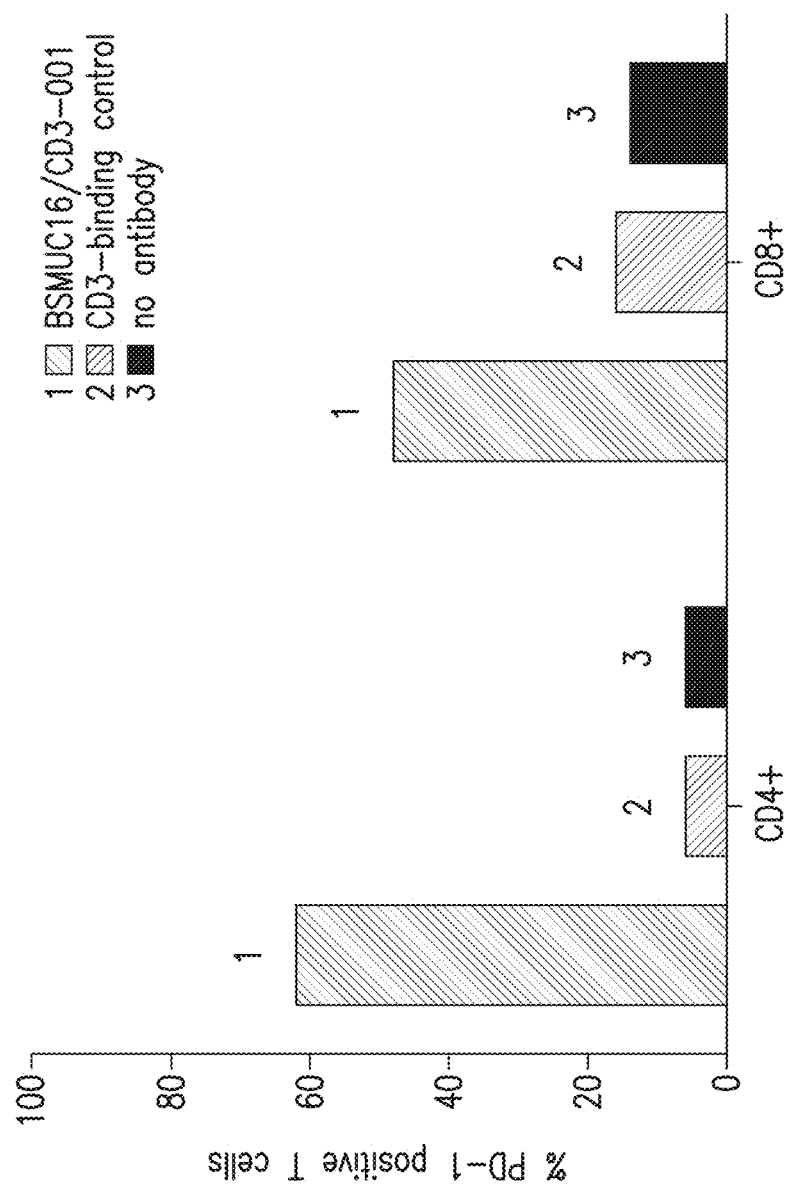
FIG. 3 illustrates the impact of T cell incubation with BSMUC16/CD3-001 on the percentage of PD-1 positive T cells.

PD-1 expression was assessed by incubating cells with directly conjugated antibodies to CD2, CD4, CD8, and PD-1 by reporting the percent of PD-1/CD4 positive T cells or PD-1/CD8 positive T cells out of total T cells (CD2+). Incubation with BSMUC16/CD3-001 increased the percentage of PD-1+ T cells by more than 10-fold (CD4+ T cells) or more than 3-fold (CD8+ T cells) compared to controls. Results are shown in FIG. 3.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method of treating or inhibiting the growth of a MUC16-expressing tumor comprising administering to a subject in need thereof (a) a therapeutically effective amount of an antibody or antigen-binding fragment thereof that specifically binds programmed death 1 (PD-1); and (b) a therapeutically effective amount of a bispecific antibody comprising a first antigen-binding arm that specifically binds MUC16 and a second antigen-binding arm that specifically binds CD3, wherein:

(a) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34;

(b) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (c) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 3, and three light chain CDRs (B-LCDR1, B-LCDR2 and B-LCDR3) of a light chain variable region (B-LCVR) comprising the amino acid sequence of SEQ ID NO: 2.

2. The method of claim 1, wherein:

(a) the anti-PD-1 antibody is administered prior to, concurrent with or after the bispecific antibody;

(b) the anti-PD-1 antibody is administered prior to the bispecific antibody; or (c) the anti-PD-1 antibody is administered at least 1 week prior to the bispecific antibody.

3. The method of claim 1, wherein:

(a) one or more doses of the anti-PD-1 antibody are administered in combination with one or more doses of the bispecific antibody;

(b) the anti-PD-1 antibody is administered at a dose of between 0.1 mg/kg and 20 mg/kg of the subject's body weight;

(c) each dose of the anti-PD-1 antibody comprises between 10-8000 micrograms;

(d) the bispecific antibody is administered at a dose of between 0.1 mg/kg and 20 mg/kg of the subject's body weight;

(e) each dose of the bispecific antibody comprises between 10-8000 micrograms;

(f) each dose of the anti-PD-1 antibody is administered 0.5-12 weeks after the immediately preceding dose;

(g) each dose of the bispecific antibody is administered 0.5-12 weeks after the immediately preceding dose; or (h) the antibodies are administered intravenously, subcutaneously, or intraperitoneally.

4. The method of claim 1, wherein the tumor comprises a pancreatic cancer.

5. The method of claim 1, wherein the subject is resistant or inadequately responsive to, or relapsed after, prior therapy.

6. The method of claim 1, further comprising administering to the subject a third therapeutic agent or therapy, optionally wherein the third therapeutic agent or therapy is selected from the group consisting of radiation, surgery, a chemotherapeutic agent, a cancer vaccine, a PD-L1 inhibitor, a LAG-3 inhibitor, a CTLA-4 inhibitor, a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an angiopoietin-2 (Ang2) inhibitor, a transforming growth factor beta (TGF.beta.) inhibitor, an epidermal growth factor receptor (EGFR) inhibitor, an antibody to a tumor-specific antigen, *Bacillus* Calmette-Guerin vaccine, granulocyte-macrophage colony-stimulating factor, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

7. The method of claim 1, wherein the anti-PD-1 antibody, the bispecific antibody, or both, comprise a human IgG1 or IgG4 heavy chain constant region.

8. The method of claim 1, wherein:

(a) HCDR1 comprises the amino acid sequence of SEQ ID NO: 35; HCDR2 comprises the amino acid sequence of SEQ ID NO: 36; HCDR3 comprises the amino acid sequence of SEQ ID NO: 37; LCDR1 comprises the amino acid sequence of SEQ ID NO: 38; LCDR2 comprises the amino acid sequence of SEQ ID NO: 39; and LCDR3 comprises the amino acid sequence of SEQ ID NO: 40;

(b) A-HCDR1 comprises the amino acid sequence of SEQ ID NO: 8; A-HCDR2 comprises the amino acid sequence of SEQ ID NO: 9; A-HCDR3 comprises the amino acid sequence of SEQ ID NO: 10; A-LCDR1 comprises the amino acid sequence of SEQ ID NO: 11; A-LCDR2 comprises the amino acid sequence of SEQ ID NO: 12; and A-LCDR3 comprises the amino acid sequence of SEQ ID NO: 13; and (c) B-HCDR1 comprises the amino acid sequence of SEQ ID NO: 14; B-HCDR2 comprises the amino acid sequence of SEQ ID NO: 15; B-HCDR3 comprises the amino acid sequence of SEQ ID NO: 16; B-LCDR1 comprises the amino acid sequence of SEQ ID NO: 11; B-LCDR2 comprises the amino acid sequence of SEQ ID NO: 12; and B-LCDR3 comprises the amino acid sequence of SEQ ID NO: 13.

9. The method of claim 8, wherein:

(a) the HCVR comprises the amino acid sequence of SEQ ID NO: 33, and the LCVR comprises the amino acid sequence of SEQ ID NO: 34;

(b) the A-HCVR comprises the amino acid sequence of SEQ ID NO:1 and the A-LCVR comprises the amino acid sequence of SEQ ID NO:2; and (c) the B-HCVR comprises the amino acid sequence of SEQ ID NO: 3, and the B-LCVR comprises the amino acid sequence of SEQ ID NO: 2.

10. The method of claim 9, wherein:

(a) the anti-PD-1 antibody comprises a heavy chain comprising the amino acid sequence of SEQ ID NO: 41, and a light chain comprising the amino acid sequence of SEQ ID NO: 42;

(b) the first antigen binding arm of the bispecific antibody comprises a heavy chain comprising the amino acid sequence of SEQ ID NO: 29, and a light chain comprising the amino acid sequence of SEQ ID NO: 30; and (c) the second antigen binding arm of the bispecific antibody comprises a heavy chain comprising the amino acid sequence of SEQ ID NO: 31, and a light chain comprising the amino acid sequence of SEQ ID NO: 30.

11. The method of claim 1, wherein the tumor comprises an ovarian cancer.

12. A method of treating or inhibiting the growth of a MUC16-expressing tumor comprising administering to a subject in need thereof (a) a therapeutically effective amount of an antibody or antigen-binding fragment thereof that specifically binds programmed death 1 (PD-1); and (b) a therapeutically effective amount of a bispecific antibody comprising a first antigen-binding arm that specifically binds MUC16 and a second antigen-binding arm that specifically binds CD3, wherein:

(a) the anti-PD-1 antibody or antigen-binding fragment thereof comprises the heavy chain complementarity determining regions (HCDR1, HCDR2 and HCDR3) of a heavy chain variable region (HCVR) comprising the amino acid sequence of SEQ ID NO: 33, and three light chain complementarity determining regions (LCDR1, LCDR2 and LCDR3) of a light chain variable region (LCVR) comprising the amino acid sequence of SEQ ID NO: 34;

(b) the first antigen-binding arm of the bispecific antibody comprises three heavy chain CDRs (A-HCDR1, A-HCDR2 and A-HCDR3) of a heavy chain variable region (A-HCVR) comprising the amino acid sequence of SEQ ID NO: 1 and three light chain CDRs (A-LCDR1, A-LCDR2 and A-LCDR3) of a light chain variable region (A-LCVR) comprising the amino acid sequence of SEQ ID NO: 2; and (c) the second antigen-binding arm of the bispecific antibody comprises three heavy chain CDRs (B-HCDR1, B-HCDR2 and B-HCDR3) of a heavy chain variable region (B-HCVR) comprising the amino acid sequence of SEQ ID NO: 7, and three light chain CDRs (B-LCDR1, B-LCDR2 and B-LCDR3) of a light chain variable region (B-LCVR) comprising the amino acid sequence of SEQ ID NO: 2.

13. The method of claim 12, wherein:
(a) HCDR1 comprises the amino acid sequence of SEQ ID NO: 35; HCDR2 comprises the amino acid sequence of SEQ ID NO: 36; HCDR3 comprises the amino acid sequence of SEQ ID NO: 37; LCDR1 comprises the amino acid sequence of SEQ ID NO: 38; LCDR2 comprises the amino acid sequence of SEQ ID NO: 39; and LCDR3 comprises the amino acid sequence of SEQ ID NO: 40;
(b) A-HCDR1 comprises the amino acid sequence of SEQ ID NO: 8; A-HCDR2 comprises the amino acid sequence of SEQ ID NO: 9; A-HCDR3 comprises the amino acid sequence of SEQ ID NO: 10; A-LCDR1 comprises the amino acid sequence of SEQ ID NO: 11; A-LCDR2 comprises the amino acid sequence of SEQ ID NO: 12; and A-LCDR3 comprises the amino acid sequence of SEQ ID NO: 13; and
(c) B-HCDR1 comprises the amino acid sequence of SEQ ID NO: 26; B-HCDR2 comprises the amino acid sequence of SEQ ID NO: 27; B-HCDR3 comprises the amino acid sequence of SEQ ID NO: 28; B-LCDR1 comprises the amino acid sequence of SEQ ID NO: 11; B-LCDR2 comprises the amino acid sequence of SEQ ID NO: 12; and B-LCDR3 comprises the amino acid sequence of SEQ ID NO: 13.

14. The method of claim 13, wherein:
(a) the HCVR comprises the amino acid sequence of SEQ ID NO: 33, and the LCVR comprises the amino acid sequence of SEQ ID NO: 34;
(b) the A-HCVR comprises the amino acid sequence of SEQ ID NO:1 and the A-LCVR comprises the amino acid sequence of SEQ ID NO:2; and
(c) the B-HCVR comprises the amino acid sequence of SEQ ID NO: 7, and the B-LCVR comprises the amino acid sequence of SEQ ID NO: 2.

15. The method of claim 14, wherein:
(a) the anti-PD-1 antibody comprises a heavy chain comprising the amino acid sequence of SEQ ID NO: 41, and a light chain comprising the amino acid sequence of SEQ ID NO: 42;
(b) the first antigen binding arm of the bispecific antibody comprises a heavy chain comprising the amino acid sequence of SEQ ID NO: 29, and a light chain comprising the amino acid sequence of SEQ ID NO: 30; and
(c) the second antigen binding arm of the bispecific antibody comprises a heavy chain comprising the amino acid sequence of SEQ ID NO: 32, and a light chain comprising the amino acid sequence of SEQ ID NO: 30.

16. The method of claim 12, wherein the tumor comprises an ovarian cancer.

17. The method of claim 12, wherein:
(a) the anti-PD-1 antibody is administered prior to, concurrent with or after the bispecific antibody;
(b) the anti-PD-1 antibody is administered prior to the bispecific antibody; or
(c) the anti-PD-1 antibody is administered at least 1 week prior to the bispecific antibody.

18. The method of claim 12, wherein:
(a) one or more doses of the anti-PD-1 antibody are administered in combination with one or more doses of the bispecific antibody;
(b) the anti-PD-1 antibody is administered at a dose of between 0.1 mg/kg and 20 mg/kg of the subject's body weight;
(c) each dose of the anti-PD-1 antibody comprises between 10-8000 micrograms;
(d) the bispecific antibody is administered at a dose of between 0.1 mg/kg and 20 mg/kg of the subject's body weight;
(e) each dose of the bispecific antibody comprises between 10-8000 micrograms;
(f) each dose of the anti-PD-1 antibody is administered 0.5-12 weeks after the immediately preceding dose;
(g) each dose of the bispecific antibody is administered 0.5-12 weeks after the immediately preceding dose; or
(h) the antibodies are administered intravenously, subcutaneously, or intraperitoneally.

19. The method of claim 12, wherein the tumor comprises a pancreatic cancer.

20. The method of claim 12, wherein the subject is resistant or inadequately responsive to, or relapsed after, prior therapy.

21. The method of claim 12, further comprising administering to the subject a third therapeutic agent or therapy, optionally wherein the third therapeutic agent or therapy is selected from the group consisting of radiation, surgery, a chemotherapeutic agent, a cancer vaccine, a PD-L1 inhibitor, a LAG-3 inhibitor, a CTLA-4 inhibitor, a TIM3 inhibitor, a BTLA inhibitor, a TIGIT inhibitor, a CD47 inhibitor, an indoleamine-2,3-dioxygenase (IDO) inhibitor, a vascular endothelial growth factor (VEGF) antagonist, an angiopoietin-2 (Ang2) inhibitor, a transforming growth factor beta (TGF.beta.) inhibitor, an epidermal growth factor receptor (EGFR) inhibitor, an antibody to a tumor-specific antigen, *Bacillus* Calmette-Guerin vaccine, granulocyte-macrophage colony-stimulating factor, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement.

22. The method of claim 12, wherein the anti-PD-1 antibody, the bispecific antibody, or both, comprise a human IgG1 or IgG4 heavy chain constant region.

\* \* \* \* \*

SEQUENCE LISTING

<160> NUMBER OF SEQ ID NOS: 42

<210> SEQ ID NO 1
<211> LENGTH: 117
<212> TYPE: PRT
<213> ORGANISM: Artificial Sequence
<220> FEATURE:
<223> OTHER INFORMATION: anti-MUC16 HCVR

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Ile
        35                  40                  45

Ser Tyr Ile Ser Gly Arg Gly Ser Thr Ile Phe Tyr Ala Asp Ser Val
    50                  55                  60

Lys Gly Arg Ile Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Val Lys Asp Arg Gly Gly Tyr Ser Pro Tyr Trp Gly Gln Gly Thr Leu
            100                 105                 110

Val Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: anti-MUC16 and anti-CD3 LCVR

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 3
<211> LENGTH: 124
<212> TYPE: PRT
<213> ORGANISM: Artificial Sequence
<220> FEATURE:
<223> OTHER INFORMATION: CD3-VH-G

<400> SEQUENCE: 3

Glu Val Gln Leu Val Glu Ser Gly Gly Gly Leu Val Gln Pro Gly Arg
1               5                   10                  15

-continued

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
            115                 120

<210> SEQ ID NO 4
<211> LENGTH: 124
<212> TYPE: PRT
<213> ORGANISM: Artificial Sequence
<220> FEATURE:
<223> OTHER INFORMATION: CD3-VH-G5

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
            115                 120

<210> SEQ ID NO 5
<211> LENGTH: 124
<212> TYPE: PRT
<213> ORGANISM: Artificial Sequence
<220> FEATURE:
<223> OTHER INFORMATION: CD3-VH-G9

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Leu Tyr Tyr Cys
                    85                  90                  95

Ala Lys Asp Gly Ser Gly Tyr Gly Lys Phe Tyr His Tyr Gly Leu Asp
                100                 105                 110

Val Trp Gly Gln Gly Thr Thr Val Thr Val Ser Ser
            115                 120
```

<210> SEQ ID NO 6
<211> LENGTH: 124
<212> TYPE: PRT
<213> ORGANISM: Artificial Sequence
<220> FEATURE:
<223> OTHER INFORMATION: CD3-VH-G10

<400> SEQUENCE: 6

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Leu Asp
            100                 105                 110

Val Trp Gly Gln Gly Thr Thr Val Thr Val Ser Ser
        115                 120
```

<210> SEQ ID NO 7
<211> LENGTH: 124
<212> TYPE: PRT
<213> ORGANISM: Artificial Sequence
<220> FEATURE:
<223> OTHER INFORMATION: CD3-VH-G20

<400> SEQUENCE: 7

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120
```

```
<210> SEQ ID NO 8
<211> LENGTH: 8
<212> TYPE: PRT
<213> ORGANISM: Artificial Sequence
<220> FEATURE:
<223> OTHER INFORMATION: anti-MUC16 HCDR1

<400> SEQUENCE: 8

Gly Phe Thr Phe Ser Asn Tyr Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: anti-MUC16 HCDR2

<400> SEQUENCE: 9

Ile Ser Gly Arg Gly Ser Thr Ile
1               5

<210> SEQ ID NO 10
<211> LENGTH: 10
<212> TYPE: PRT
<213> ORGANISM: Artificial Sequence
<220> FEATURE:
<223> OTHER INFORMATION: anti-MUC16 HCDR3

<400> SEQUENCE: 10

Val Lys Asp Arg Gly Gly Tyr Ser Pro Tyr
1               5                   10

<210> SEQ ID NO 11
<211> LENGTH: 6
<212> TYPE: PRT
<213> ORGANISM: Artificial Sequence
<220> FEATURE:
<223> OTHER INFORMATION: anti-MUC16 and anti-CD3 LCDR1

<400> SEQUENCE: 11

Gln Ser Ile Ser Thr Tyr
1               5

<210> SEQ ID NO 12
<211> LENGTH: 3
<212> TYPE: PRT
<213> ORGANISM: Artificial Sequence
<220> FEATURE:
<223> OTHER INFORMATION: anti-MUC16 and anti-CD3 LCDR2

<400> SEQUENCE: 12

Thr Ala Ser
1

<210> SEQ ID NO 13
<211> LENGTH: 10
<212> TYPE: PRT
<213> ORGANISM: Artificial Sequence
<220> FEATURE:
<223> OTHER INFORMATION: anti-MUC16 and anti-CD3 LCDR3

<400> SEQUENCE: 13

Gln Gln Ser Tyr Ser Thr Pro Pro Ile Thr
1               5                   10
```

```
<210> SEQ ID NO 14
<211> LENGTH: 8
<212> TYPE: PRT
<213> ORGANISM: Artificial Sequence
<220> FEATURE:
<223> OTHER INFORMATION: CD3-VH-G HCDR1

<400> SEQUENCE: 14

Gly Phe Thr Phe Asp Asp Tyr Ser
1               5

<210> SEQ ID NO 15
<211> LENGTH: 8
<212> TYPE: PRT
<213> ORGANISM: Artificial Sequence
<220> FEATURE:
<223> OTHER INFORMATION: CD3-VH-G HCDR2

<400> SEQUENCE: 15

Ile Ser Trp Asn Ser Gly Ser Lys
1               5

<210> SEQ ID NO 16
<211> LENGTH: 17
<212> TYPE: PRT
<213> ORGANISM: Artificial Sequence
<220> FEATURE:
<223> OTHER INFORMATION: CD3-VH-G HCDR3

<400> SEQUENCE: 16

Ala Lys Tyr Gly Ser Gly Tyr Gly Lys Phe Tyr His Tyr Gly Leu Asp
1               5                   10                  15

Val

<210> SEQ ID NO 17
<211> LENGTH: 8
<212> TYPE: PRT
<213> ORGANISM: Artificial Sequence
<220> FEATURE:
<223> OTHER INFORMATION: CD3-VH-G5 HCDR1

<400> SEQUENCE: 17

Gly Phe Thr Phe Asp Asp Tyr Ser
1               5

<210> SEQ ID NO 18
<211> LENGTH: 8
<212> TYPE: PRT
<213> ORGANISM: Artificial Sequence
<220> FEATURE:
<223> OTHER INFORMATION: CD3-VH-G5 HCDR2

<400> SEQUENCE: 18

Ile Ser Trp Asn Ser Gly Ser Ile
1               5

<210> SEQ ID NO 19
<211> LENGTH: 17
<212> TYPE: PRT
<213> ORGANISM: Artificial Sequence
<220> FEATURE:
<223> OTHER INFORMATION: CD3-VH-G5 HCDR3

<400> SEQUENCE: 19

Ala Lys Asp Gly Ser Gly Tyr Gly Lys Phe Tyr Tyr Tyr Gly Met Asp
1               5                   10                  15
```

Val

<210> SEQ ID NO 20
<211> LENGTH: 8
<212> TYPE: PRT
<213> ORGANISM: Artificial Sequence
<220> FEATURE:
<223> OTHER INFORMATION: CD3-VH-G9 HCDR1

<400> SEQUENCE: 20

Gly Phe Thr Phe Asp Asp Tyr Ser
1               5

<210> SEQ ID NO 21
<211> LENGTH: 8
<212> TYPE: PRT
<213> ORGANISM: Artificial Sequence
<220> FEATURE:
<223> OTHER INFORMATION: CD3-VH-G9 HCDR2

<400> SEQUENCE: 21

Ile Ser Trp Asn Ser Gly Ser Lys
1               5

<210> SEQ ID NO 22
<211> LENGTH: 17
<212> TYPE: PRT
<213> ORGANISM: Artificial Sequence
<220> FEATURE:
<223> OTHER INFORMATION: CD3-VH-G9 HCDR3

<400> SEQUENCE: 22

Ala Lys Asp Gly Ser Gly Tyr Gly Lys Phe Tyr His Tyr Gly Leu Asp
1               5                   10                  15
Val

<210> SEQ ID NO 23
<211> LENGTH: 8
<212> TYPE: PRT
<213> ORGANISM: Artificial Sequence
<220> FEATURE:
<223> OTHER INFORMATION: CD3-VH-G10 HCDR1

<400> SEQUENCE: 23

Gly Phe Thr Phe Asp Asp Tyr Ser
1               5

<210> SEQ ID NO 24
<211> LENGTH: 8
<212> TYPE: PRT
<213> ORGANISM: Artificial Sequence
<220> FEATURE:
<223> OTHER INFORMATION: CD3-VH-G10 HCDR2

<400> SEQUENCE: 24

Ile Ser Trp Asn Ser Gly Ser Lys
1               5

<210> SEQ ID NO 25
<211> LENGTH: 17
<212> TYPE: PRT
<213> ORGANISM: Artificial Sequence
<220> FEATURE:
<223> OTHER INFORMATION: CD3-VH-G10 HCDR3

<400> SEQUENCE: 25

```
Ala Lys Tyr Gly Ser Gly Tyr Gly Lys Phe Tyr Tyr Tyr Gly Leu Asp
1               5                   10                  15

Val
```

<210> SEQ ID NO 26
<211> LENGTH: 8
<212> TYPE: PRT
<213> ORGANISM: Artificial Sequence
<220> FEATURE:
<223> OTHER INFORMATION: CD3-VH-G20 HCDR1

<400> SEQUENCE: 26

```
Gly Phe Thr Phe Asp Asp Tyr Ser
1               5
```

<210> SEQ ID NO 27
<211> LENGTH: 8
<212> TYPE: PRT
<213> ORGANISM: Artificial Sequence
<220> FEATURE:
<223> OTHER INFORMATION: CD3-VH-G20 HCDR2

<400> SEQUENCE: 27

```
Ile Ser Trp Asn Ser Gly Ser Ile
1               5
```

<210> SEQ ID NO 28
<211> LENGTH: 17
<212> TYPE: PRT
<213> ORGANISM: Artificial Sequence
<220> FEATURE:
<223> OTHER INFORMATION: CD3-VH-G20 HCDR3

<400> SEQUENCE: 28

```
Ala Lys Tyr Gly Ser Gly Tyr Gly Lys Phe Tyr Tyr Tyr Gly Met Asp
1               5                   10                  15

Val
```

<210> SEQ ID NO 29
<211> LENGTH: 443
<212> TYPE: PRT
<213> ORGANISM: Artificial Sequence
<220> FEATURE:
<223> OTHER INFORMATION: anti-MUC16 HC
      aa 1-117: Variable region
      aa 118-443: Constant region

<400> SEQUENCE: 29

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Ile
        35                  40                  45

Ser Tyr Ile Ser Gly Arg Gly Ser Thr Ile Phe Tyr Ala Asp Ser Val
    50                  55                  60

Lys Gly Arg Ile Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Val Lys Asp Arg Gly Gly Tyr Ser Pro Tyr Trp Gly Gln Gly Thr Leu
            100                 105                 110
```

```
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 30
<211> LENGTH: 215
<212> TYPE: PRT
<213> ORGANISM: Artificial Sequence
<220> FEATURE:
<223> OTHER INFORMATION: anti-MUC16 and anti-CD3 LC
      aa 1-108: Variable region
      aa 109-215: Constant region

<400> SEQUENCE: 30

Asp Ile Gln Met Thr Gln Ser Pro Ser Ser Leu Ser Ala Ser Val Gly
                5                   10                  15

Asp Arg Val Thr Ile Thr Cys Arg Ala Ser Gln Ser Ile Ser Thr Tyr
```

```
            20                  25                  30
Leu Asn Trp Tyr Gln Gln Lys Pro Gly Lys Ala Pro Lys Leu Leu Ile
            35                  40                  45

Tyr Thr Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 31
<211> LENGTH: 450
<212> TYPE: PRT
<213> ORGANISM: Artificial Sequence
<220> FEATURE:
<223> OTHER INFORMATION: anti-CD3-G HC
      aa 1-124: Variable region
      aa 125-450: Constant region

<400> SEQUENCE: 31

Glu Val Gln Leu Val Glu Ser Gly Gly Gly Leu Val Gln Pro Gly Arg
                  5                  10                  15

Ser Leu Arg Leu Ser Cys Ala Ala Ser Gly Phe Thr Phe Asp Asp Tyr
             20                  25                  30

Ser Met His Trp Val Arg Gln Ala Pro Gly Lys Gly Leu Glu Trp Val
         35                  40                  45

Ser Gly Ile Ser Trp Asn Ser Gly Ser Lys Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Tyr Gly Ser Gly Tyr Gly Lys Phe Tyr His Tyr Gly Leu Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160
```

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
            210                 215                 220

Lys Tyr Gly Pro Pro Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn Arg Phe Thr Gln Lys Ser Leu Ser Leu Ser Pro
            435                 440                 445

Gly Lys
    450

<210> SEQ ID NO 32
<211> LENGTH: 450
<212> TYPE: PRT
<213> ORGANISM: Artificial Sequence
<220> FEATURE:
<223> OTHER INFORMATION: anti-CD3-G20 HC
      aa 1-124: Variable region
      aa 125-450: Constant region

<400> SEQUENCE: 32

Glu Val Gln Leu Val Glu Ser Gly Gly Gly Leu Val Gln Pro Gly Arg
                5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
            35                  40                  45

```
Ser Gly Ile Ser Trp Asn Ser Gly Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Tyr Gly Ser Gly Tyr Gly Lys Phe Tyr Tyr Gly Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn Arg Phe Thr Gln Lys Ser Leu Ser Leu Ser Pro
            435                 440                 445

Gly Lys
450
```

```
<210> SEQ ID NO 33
<211> LENGTH: 117
<212> TYPE: PRT
<213> ORGANISM: Artificial Sequence
<220> FEATURE:
<223> OTHER INFORMATION: anti-PD-1 HCVR

<400> SEQUENCE: 33

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: anti-PD-1 LCVR

<400> SEQUENCE: 34

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg
            100                 105

<210> SEQ ID NO 35
<211> LENGTH: 8
<212> TYPE: PRT
<213> ORGANISM: Artificial Sequence
<220> FEATURE:
<223> OTHER INFORMATION: anti-PD-1 HCDR1

<400> SEQUENCE: 35

Gly Phe Thr Phe Ser Asn Phe Gly
1               5

<210> SEQ ID NO 36
```

```
<211> LENGTH: 8
<212> TYPE: PRT
<213> ORGANISM: Artificial Sequence
<220> FEATURE:
<223> OTHER INFORMATION: anti-PD-1 HCDR2

<400> SEQUENCE: 36

Ile Ser Gly Gly Gly Arg Asp Thr
1               5

<210> SEQ ID NO 37
<211> LENGTH: 10
<212> TYPE: PRT
<213> ORGANISM: Artificial Sequence
<220> FEATURE:
<223> OTHER INFORMATION: anti-PD-1 HCDR3

<400> SEQUENCE: 37

Val Lys Trp Gly Asn Ile Tyr Phe Asp Tyr
1               5                   10

<210> SEQ ID NO 38
<211> LENGTH: 6
<212> TYPE: PRT
<213> ORGANISM: Artificial Sequence
<220> FEATURE:
<223> OTHER INFORMATION: anti-PD-1 LCDR1

<400> SEQUENCE: 38

Leu Ser Ile Asn Thr Phe
1               5

<210> SEQ ID NO 39
<211> LENGTH: 3
<212> TYPE: PRT
<213> ORGANISM: Artificial Sequence
<220> FEATURE:
<223> OTHER INFORMATION: anti-PD-1 LCDR2

<400> SEQUENCE: 39

Ala Ala Ser
1

<210> SEQ ID NO 40
<211> LENGTH: 9
<212> TYPE: PRT
<213> ORGANISM: Artificial Sequence
<220> FEATURE:
<223> OTHER INFORMATION: anti-PD-1 LCDR3

<400> SEQUENCE: 40

Gln Gln Ser Ser Asn Thr Pro Phe Thr
1               5

<210> SEQ ID NO 41
<211> LENGTH: 444
<212> TYPE: PRT
<213> ORGANISM: Artificial Sequence
<220> FEATURE:
<223> OTHER INFORMATION: anti-PD-1 HC
      aa 1-117: Variable region
      aa 118-444: Constant region

<400> SEQUENCE: 41

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
```

```
            20                  25                  30
Gly Met Thr Trp Val Arg Gln Ala Pro Gly Lys Gly Leu Glu Trp Val
                35                  40                  45

Ser Gly Ile Ser Gly Gly Arg Asp Thr Tyr Phe Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Gly Glu Asp Thr Ala Val Tyr Tyr Cys
                 85                  90                  95

Val Lys Trp Gly Asn Ile Tyr Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Cys Ser Arg Ser Thr Ser Glu Ser Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
                195                 200                 205

Thr Lys Val Asp Lys Arg Val Glu Ser Lys Tyr Gly Pro Pro Cys Pro
                210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440
```

```
<210> SEQ ID NO 42
<211> LENGTH: 214
<212> TYPE: PRT
<213> ORGANISM: Artificial Sequence
<220> FEATURE:
<223> OTHER INFORMATION: anti-PD-1 LC
      aa 1-108: Variable region
      aa 109-214: Constant region

<400> SEQUENCE: 42

Asp Ile Gln Met Thr Gln Ser Pro Ser Ser Leu Ser Ala Ser Val Gly
1               5                   10                  15

Asp Ser Ile Thr Ile Thr Cys Arg Ala Ser Leu Ser Ile Asn Thr Phe
            20                  25                  30

Leu Asn Trp Tyr Gln Gln Lys Pro Gly Lys Ala Pro Asn Leu Leu Ile
        35                  40                  45

Tyr Ala Ala Ser Ser Leu His Gly Gly Val Pro Ser Arg Phe Ser Gly
50                  55                  60

Ser Gly Ser Gly Thr Asp Phe Thr Leu Thr Ile Arg Thr Leu Gln Pro
65                  70                  75                  80

Glu Asp Phe Ala Thr Tyr Tyr Cys Gln Gln Ser Ser Asn Thr Pro Phe
                85                  90                  95

Thr Phe Gly Pro Gly Thr Val Val Asp Phe Arg Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```